(12) United States Patent
Benner

(10) Patent No.: US 8,153,361 B1
(45) Date of Patent: Apr. 10, 2012

(54) DYNAMIC AND COMBINATORIAL SYNTHESIS OF POLYMERASE PRIMERS

(76) Inventor: Steven Albert Benner, Gainesville, FL (US)

( * ) Notice: Subject to any disclaimer, the term of this patent is extended or adjusted under 35 U.S.C. 154(b) by 1188 days.

(21) Appl. No.: 11/702,327

(22) Filed: Feb. 5, 2007

Related U.S. Application Data

(60) Provisional application No. 60/765,658, filed on Feb. 6, 2006.

(51) Int. Cl.
C12Q 1/68 (2006.01)
C12P 19/34 (2006.01)
C07H 21/00 (2006.01)

(52) U.S. Cl. .......... 435/6; 435/91.1; 526/23.1; 526/24.3

(58) Field of Classification Search .............. 435/6, 91.1; 536/23.1, 24.3
See application file for complete search history.

(56) References Cited

U.S. PATENT DOCUMENTS 5,686,243 A * 11/1997 Royer et al. ................. 435/6.12

FOREIGN PATENT DOCUMENTS

WO WO 0061775 A1 * 10/2000

OTHER PUBLICATIONS

Mirkin, C. A., Letsinger, R. L., Mucic, R. D., Storhoff, J. J. (1996) A DNA-based method for rationally assembling nanoparticles into macroscopic materials. Nature, vol. 382, 607-609.

Mag, M., Luking, S., Engels, J. W. (1996) Synthesis and selective cleavage of an oligodeoxynucleotide containing a bridged internucleotide 5'-phosphorothioate linkage. Nucleic Acids Research, vol. 19, 1437-1440.

Leal, N. A., Sukeda, M., Benner, S. A. (2006) Dynamic assembly of primers on nucleic acid templates. Nucleic Acids Research, 34, 4702-4710.

* cited by examiner

Primary Examiner — Jezia Riley

(57) ABSTRACT

This invention relates to the field of nucleic acid chemistry, more specifically to compositions of matter that are nucleic acid analogs, and processes that use them. Still more specifically, these compositions comprise two fragments of DNA-like molecules, each having one or more ends modified to carry a reactive group, where the reactive group on one fragment can form a transient covalent bond with the reactive group on the other under conditions of dynamic equilibrium to form a composite, where the composite can then bind to a target oligonucleotide, such as a DNA or RNA molecule. Most specifically, once the transient covalent bond forms, the composite serves as a primer for a template-directed polymerization using a DNA polymerase, an RNA polymerase, or a reverse transcriptase. Once incorporated, the epimerization causes the base pair to be destabilized, the duplex containing the epimerized nucleoside to likewise be destabilized, and the double strand to then disassociate. This leaves the template available to template the synthesis of another complementary oligonucleotide containing the epimerizing base.

9 Claims, 17 Drawing Sheets

Q = OH, NHR
R = H, substituent (a) TBSCl, py, 0°C to rt; (b) Thiocarbonyldiimidazole, PhH, reflux; (c) Allyltributyltin, AIBN, PhH, reflux; (d) TBAF, THF
(e) 2-Cyanoethyl-N,N-diisopropylchlorophosphoramidite, diisopropylethylamine, CH₂Cl₂

(a) OsO₄, NMO, H₂O; (b) NaIO₄, H₂O; (c) O-benzylhydroxylamine hydrochloride, TEAA; (d) template (21), NaCl, phosphate buffer (pH 6), then NaCNBH₃

```
                              SEQUENCE LISTING

<160> NUMBER OF SEQ ID NOS: 22

<210> SEQ ID NO 1
<211> LENGTH: 38
<212> TYPE: DNA
<213> ORGANISM: Artificial Sequence
<220> FEATURE:
<223> OTHER INFORMATION: Synthetic

<400> SEQUENCE: 1
cggtttatga ggtttgggaa aagtgtagat ggtgatgt                                38

<210> SEQ ID NO 2
<211> LENGTH: 38
<212> TYPE: DNA
<213> ORGANISM: Artificial Sequence
<220> FEATURE:
<223> OTHER INFORMATION: Synthetic

<400> SEQUENCE: 2
cggtttatga gatttgggaa aagtgtagat ggtgatgt                                38

<210> SEQ ID NO 3
<211> LENGTH: 38
<212> TYPE: DNA
<213> ORGANISM: Artificial Sequence
<220> FEATURE:
<223> OTHER INFORMATION: Synthetic

<400> SEQUENCE: 3
cggtttatga gttttgggaa aagtgtagat ggtgatgt                                38

<210> SEQ ID NO 4
<211> LENGTH: 38
<212> TYPE: DNA
<213> ORGANISM: Artificial Sequence
<220> FEATURE:
<223> OTHER INFORMATION: Synthetic

<400> SEQUENCE: 4
cggtttatga gctttgggaa aagtgtagat ggtgatgt                                38

<210> SEQ ID NO 5
<211> LENGTH: 38
<212> TYPE: DNA
<213> ORGANISM: Artificial Sequence
<220> FEATURE:
```

<223> OTHER INFORMATION: Synthetic

<400> SEQUENCE: 5
cggtttatga ggttcgggaa aagtgtagat ggtgatgt                                   38

<210> SEQ ID NO 6
<211> LENGTH: 38
<212> TYPE: DNA
<213> ORGANISM: Artificial Sequence
<220> FEATURE:
<223> OTHER INFORMATION: Synthetic

<400> SEQUENCE: 6
cggtttatga ggttggggaa aagtgtagat ggtgatgt                                   38

<210> SEQ ID NO 7
<211> LENGTH: 38
<212> TYPE: DNA
<213> ORGANISM: Artificial Sequence
<220> FEATURE:
<223> OTHER INFORMATION: Synthetic

<400> SEQUENCE: 7
cggtttatga ggttagggaa aagtgtagat ggtgatgt                                   38

<210> SEQ ID NO 8
<211> LENGTH: 38
<212> TYPE: DNA
<213> ORGANISM: Artificial Sequence
<220> FEATURE:
<223> OTHER INFORMATION: Synthetic

<400> SEQUENCE: 8
cggtttatga ggtttggga aagtgtagat ggtgatgt                                    38

<210> SEQ ID NO 9
<211> LENGTH: 38
<212> TYPE: DNA
<213> ORGANISM: Artificial Sequence
<220> FEATURE:
<223> OTHER INFORMATION: Synthetic

<400> SEQUENCE: 9
cggtttatga ggtttgggca aagtgtagat ggtgatgt                                   38

<210> SEQ ID NO 10
<211> LENGTH: 38
<212> TYPE: DNA
<213> ORGANISM: Artificial Sequence
<220> FEATURE:
<223> OTHER INFORMATION: Synthetic

<400> SEQUENCE: 10
cggtttatga ggtttgggta aagtgtagat ggtgatgt                                   38

<210> SEQ ID NO 11
<211> LENGTH: 38
<212> TYPE: DNA
<213> ORGANISM: Artificial Sequence
<220> FEATURE:
<223> OTHER INFORMATION: Synthetic

<400> SEQUENCE: 11
cggtttatga ggtttgggag aagtgtagat ggtgatgt                                   38

<210> SEQ ID NO 12

```
<211> LENGTH: 38
<212> TYPE: DNA
<213> ORGANISM: Artificial Sequence
<220> FEATURE:
<223> OTHER INFORMATION: Synthetic

<400> SEQUENCE: 12
cggtttatga ggtttgggac aagtgtagat ggtgatgt                            38

<210> SEQ ID NO 13
<211> LENGTH: 38
<212> TYPE: DNA
<213> ORGANISM: Artificial Sequence
<220> FEATURE:
<223> OTHER INFORMATION: Synthetic

<400> SEQUENCE: 13
cggtttatga ggtttgggat aagtgtagat ggtgatgt                            38

<210> SEQ ID NO 14
<211> LENGTH: 38
<212> TYPE: DNA
<213> ORGANISM: Artificial Sequence
<220> FEATURE:
<223> OTHER INFORMATION: Synthetic

<400> SEQUENCE: 14
cggtttatga ggtttgggaa aaatgtagat ggtgatgt                            38

<210> SEQ ID NO 15
<211> LENGTH: 38
<212> TYPE: DNA
<213> ORGANISM: Artificial Sequence
<220> FEATURE:
<223> OTHER INFORMATION: Synthetic

<400> SEQUENCE: 15
cggtttatga ggtttgggaa aattgtagat ggtgatgt                            38

<210> SEQ ID NO 16
<211> LENGTH: 38
<212> TYPE: DNA
<213> ORGANISM: Artificial Sequence
<220> FEATURE:
<223> OTHER INFORMATION: Synthetic

<400> SEQUENCE: 16
cggtttatga ggtttgggaa aactgtagat ggtgatgt                            38

<210> SEQ ID NO 17
<211> LENGTH: 38
<212> TYPE: DNA
<213> ORGANISM: Artificial Sequence
<220> FEATURE:
<223> OTHER INFORMATION: Synthetic

<400> SEQUENCE: 17
cggtttatga ggtttgggaa aagtgtggat ggtgatgt                            38

<210> SEQ ID NO 18
<211> LENGTH: 38
<212> TYPE: DNA
<213> ORGANISM: Artificial Sequence
<220> FEATURE:
<223> OTHER INFORMATION: Synthetic

<400> SEQUENCE: 18
```

-continued

```
cggtttatga ggtttgggaa aagtgtcgat ggtgatgt                              38

<210> SEQ ID NO 19
<211> LENGTH: 38
<212> TYPE: DNA
<213> ORGANISM: Artificial Sequence
<220> FEATURE:
<223> OTHER INFORMATION: Synthetic

<400> SEQUENCE: 19
cggtttatga ggtttgggaa aagtgttgat ggtgatgt                              38

<210> SEQ ID NO 20
<211> LENGTH: 38
<212> TYPE: DNA
<213> ORGANISM: Artificial Sequence
<220> FEATURE:
<223> OTHER INFORMATION: Synthetic

<400> SEQUENCE: 20
cggtttatga ggtttgagaa aagtgtagat ggtgatgt                              38

<210> SEQ ID NO 21
<211> LENGTH: 38
<212> TYPE: DNA
<213> ORGANISM: Artificial Sequence
<220> FEATURE:
<223> OTHER INFORMATION: Synthetic

<400> SEQUENCE: 21
cggtttatga ggtttgtgaa aagtgtagat ggtgatgt                              38

<210> SEQ ID NO 22
<211> LENGTH: 38
<212> TYPE: DNA
<213> ORGANISM: Artificial Sequence
<220> FEATURE:
<223> OTHER INFORMATION: Synthetic

<400> SEQUENCE: 22
cggtttatga ggtttgcgaa aagtgtagat ggtgatgt                              38
```

DYNAMIC AND COMBINATORIAL SYNTHESIS OF POLYMERASE PRIMERS

CROSS REFERENCE TO RELATED APPLICATIONS

This application claims benefit of provisional patent application 60/765/658, filed Feb. 6, 2006.

STATEMENT OF RIGHTS TO INVENTIONS MADE UNDER FEDERALLY-SPONSORED RESEARCH

This invention was made with government support under 1R41GM079897 awarded by NIH. The government has certain rights in the invention.

FIELD

This invention relates to the field of nucleic acid chemistry, more specifically to the field of compositions and processes that can be used to detect nucleic acid analogs. More specifically, this invention relates to compositions that copy oligonucleotides with the specificity of a primer that covers 10-16 nucleotides, but the discrimination power of a 5-8mer.

BACKGROUND

The availability of complete genome sequences has created the demand for analytical tools to detect specific nucleic acid sequences (xNAs, which include DNA and RNA) in biological mixtures. These tools are needed in the clinic, in forensics, in exploring the microbial biosphere, as part of taggant detection systems, as well as in biomedical research laboratories. In the clinic, the tools are needed to detect low levels of single DNA/RNA targets that indicate the presence of infectious disease agents or biohazards. In both the research laboratory and the clinic, tools are needed to detect single nucleotide polymorphisms, as well as tools to detect multiple xNA targets at the same time on microarrays (in expression profiles, for example) [Pom02]. The purpose of the instant invention is to provide tools for doing this.

A general paradox is associated with architectures to detect specific nucleic acids in complex biological mixtures. First, as there are $4^n$ different sequences of length n, a probe that is specific for a single sequence within a target genome having length G (nucleotides) will, on average, have a length L (nucleotides) that is given by the formula L=(log G)/0.6. Thus, for the human genome with ca. $3 \times 10^9$ nucleotides, a probe that is 16 nucleotides long will bind, on average, once to the target genome.

This type of calculation suggests that one can seek specific genes in a human genome using 16mer complements as probes. Unfortunately, for duplexes of this length under standard hybridization conditions, single mismatches depress the melting temperatures only slightly. Further, the different intrinsic affinities of the AT and GC nucleobase pairs, as well as the fact that the contribution of any nucleobase pair has a non-negligible dependence on the local sequence context, means that a duplex built from two 16mers having two mismatches can easily be more stable than a duplex built from two perfectly matched 16mers, even if they have the same overall GC/AT composition.

Of course, if the probe is shorter, then a duplex with a single mismatch will be less stable than any perfectly matched duplex. For DNA-DNA duplexes under standard conditions, this is certainly met by duplexes as short as 4 nucleobase pairs, and generally by duplexes as long as 10 nucleobase pairs. These, however, lack specificity in the human genome (a 10mer is found on average 4000 times in the human genome). Further, very short nucleotides (e.g. 4mers) are too short to truly display a "melting temperature", a sharp transition between bound and unbound states as a function of temperature. Rather, the unbinding curves have the sigmoidal shape characteristic for a binary dissociation process.

Reversible template ligation can offer a solution to this problem. This approach differs from the irreversible template ligation suggested by Kool [San04], von Kiedrowski [Sie94] [Bag96] Templates, autocatalysis and molecular replication. *Pure Appl. Chem.*, 68, 2145-2152. Ellington [Jam99] and others, in that the reversible ligation permits the system to achieve the thermodynamically preferred combination without kinetic traps.

Work by Lynn and his coworkers provides another part of the background for the instant invention [Goo92][Goo92] [Zha97][Zha01]. In 1997, Lynn and his coworkers showed that complementary oligonucleotides could be assembled using imine chemistry from fragments under conditions of dynamic equilibrium [Yun97]. They did not propose this to be done in a combinatorial sense. Rather, their goal was to model chemistry that might create artificial replicating systems, themselves models for how life might have emerged on early Earth. Thus, Lynn and his coworkers used only short trinucleotides as their fragments, and immediately captured the imine by reducing it with borohydride to give a hexamer with a central, unnatural, $CH_2$—$CH_2$—NH—$CH_2$ linker (FIG. 3). This created a stable secondary amine linker. They did not attempt to learn whether the imine formed transiently could serve as a primer.

Because Lynn and his group had the imine only transiently in hand, they could obtain only and approximate estimated the increased affinity due to the templating reaction, about a factor of 10. Further, they did not examine the infidelity of the process, the success of the process as a function of the length of the 3'- and 5'-fragments, or the fidelity of the process as a function of the length of the fragments. All are expected to be interrelated, and depend on the temperature, which will in turn be determined by the polymerase that is used to extend the fragment. This temperature must be low if reverse transcriptase is used to extend the primers (as in RNA transcription profiling, for example) or high if a thermostable DNA polymerase is used.

Of somewhat greater concern was the observation by Lynn and his coworkers that the binding of the secondary amine product obtained by the reduction of the imine to complementary DNA was lower than the binding of the analogous DNA-DNA complement [Luo98]. These authors examined the destabilization that arises from a single $CH_2$—$CH_2$—NH—$CH_2$ linker in a short oligonucleotide, which can drop $T_m$ as much as by 15° C. [Luo98]. From our work in this area [Hut02][Ben04], it is likely that the destabilization is due to the increased flexibility and complementary charge of the $CH_2$—$CH_2$—NH—$CH_2$ unit. If so, the destabilization should be less with the imine $CH_2$—CH=NH—$CH_2$ linker.

DESCRIPTION OF THE INVENTION

Figure 2:
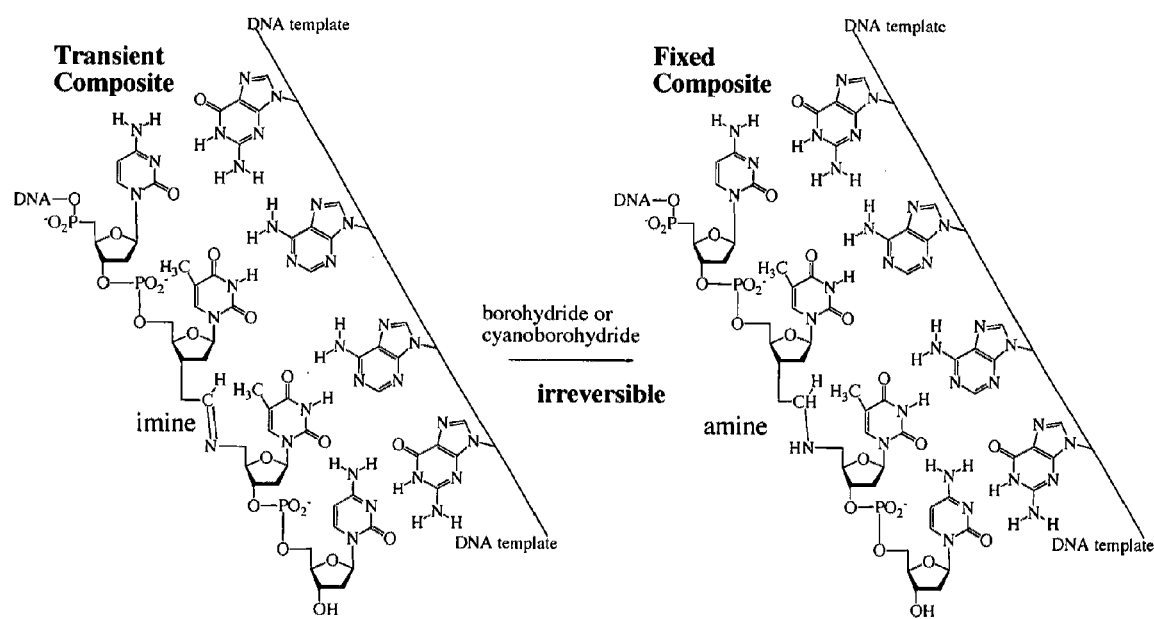
FIG. 2. The transient composite can be "fixed" by reduction of the imine linker to a secondary amine.

The goal of the instant invention is to use synthesis under conditions of dynamic equilibrium to assemble a complementary primer molecule onto a preselected xNA template, and to capture this primer not by reduction with borohydride (or an equivalent), but rather via polymerase-dependent chain extension. A further goal of the instant invention is to enable this as part of a dynamic combinatorial experiment. The essence of the instant invention is illustrated in FIG. 2. To practice the invention in a non-combinatorial sense requires the following steps:

1. Synthesize a short (4-15 nucleotides in length) DNA fragment molecule having a functional group at its 5'-terminus (the 3'-fragment), where the fragment is complementary to a preselected template molecule, which may be either a DNA or RNA molecule, or an analog of these that binds with Watson-Crick complementarity. The target and fragment molecules can, therefore, incorporate elements of an artificially expanded genetic information system [Ben04], or a universal nucleobase. The DNA fragment can be built from DNA, RNA, a 2'-O-alkylated RNA (methyl or allyl, for example), or a backbone analog of DNA, including a locked nucleic acid, bicyclonucleic acid, a peptide nucleic acid, or a glycol nucleic acid [Zha05].

2. Synthesize a short (4-15 nucleotides in length) DNA fragment molecules having a functional group at its 3'-terminal (the 5'-fragment), where the fragment is complementary to the same preselected template in a segment adjacent (in the 3'-direction) to the segment that the 3'-DNA fragment is complementary to.

3. Contact the DNA fragments with the preselected template in an incubation mixture that presents conditions where hybridization occurs, and where the functional group on the 3'-DNA fragment forms under conditions of dynamic equilibrium at covalent bond with the functional group on the 3'-DNA fragment. The product arising from the dynamical joining of the fragments is called the "composite".

4. Ensure that the dynamically formed products are able to contact an enzymatic reaction that transforms the complex that has a covalent bond, where the substrates necessary for the enzymatic reaction are present as well. We shall refer to this as "downstream processing".

In one of several implementations that this disclosure makes obvious to one of ordinary skill in the art, the functional groups are amino and formyl, the transiently formed covalent bond is an imine, and the enzymatic capture reaction is a template-directed polymerization catalyzed by a DNA polymerase, an RNA polymerase, or a reverse transcriptase, and the substrates necessary for the enzymatic reaction are nucleoside triphosphates. Specifically, the procedure of this example comprises the following steps:

1. Synthesize short (4-15 nucleotides in length) DNA fragment molecules with a 5'-terminal amino group replacing the 5'-OH group (the 3'-DNA fragment) that are complementary to a preselected template molecule, which may be either a DNA or RNA molecule, or an analog of these that binds with Watson-Crick complementarity. These molecules are known in the art; some phosphoramidites to complete a DNA synthesis with the 5'-group replaced by a 5'-amino group are commercially available.

2. Synthesize short (4-15 nucleotides in length) DNA fragment molecules with a 3'-terminal CH$_2$—CHO group (the 5'-DNA fragment) that are complementary to the preselected template. These formylated nucleosides are also known in the art [Chu89][Zha01][Goo92]; the DNA having a 3'-terminal CH$_2$—CHO group is synthesized in the 5'-to-3' direction (the opposite of that normally done in most DNA syntheses) [Bog99]. Phosphoramidites to do a DNA synthesis in this direction are commercially available.

3. Incubate the DNA fragments with the preselected template under conditions where hybridization occurs, generally with 10-200 mM NaCl or another salt, with the salt and buffer conditions chosen to allow the polymerase to be active, under directions of the manufacturer of the polymerase/reverse transcriptase used. In this process, the imine is formed in situ.

4. Incubate the DNA fragments with the preselected template under conditions where hybridization occurs in the presence of a DNA polymerase, an RNA polymerase, or a reverse transcriptase, and in the presence of the appropriate nucleoside triphosphates, under conditions where the polymerase is active as a catalyst.

Note that in the DNA, the 5'-end may be stabilized in the duplex, and retained. Upon denaturation, however, the 5'-unit joined via an imine is likely to fall away, leaving behind a product terminated with a 5' amino group. This can be used as the basis for capture.

In situ generation of primers under conditions of dynamic equilibrium is useful for a variety of purposes, including simple DNA target detection (through the incorporation of labeled triphosphates), managing repeats in DNA sequencing, detection of species such as RNAi whose presence is suspected but whose sequence is unknown, and determining the existence of specific splice sites, for example. Further, tags built from an artificially expanded genetic information system (AEGIS) [Ben04] can be appended to a fraction of the repeat elements, to permit the capture of the composite without interference by the many DNA sequences present in the assembly mixture. Using this technology, it should be possible to determine the sequence of the oligonucleotide downstream from the primer that has been assembled.

Commercial products include custom-synthesized short DNA molecules with a 5'-terminal amino groups (the 3'-DNA fragments) and DNA molecules with a 3'-terminal CH$_2$—CHO groups (the 5'-DNA fragments), building blocks for these, and kits to support DNA-TACS. Product applications include tools for specific DNA target detection, sequencing of DNA using "semi-random primers, detection of species such as RNAi whose presence is suspected but whose sequence is unknown, managing repeats in DNA sequencing, and determining the existence of specific splice sites, for example. Further, tags built from an artificially expanded genetic information system (AEGIS) [Ben04] can be appended to a fraction of the repeat elements, to permit the capture of the composite without interference by the many DNA sequences present in the assembly mixture. Using this technology, it should be possible to determine the sequence of the oligonucleotide downstream from the primer that has been assembled.

Figure 3:
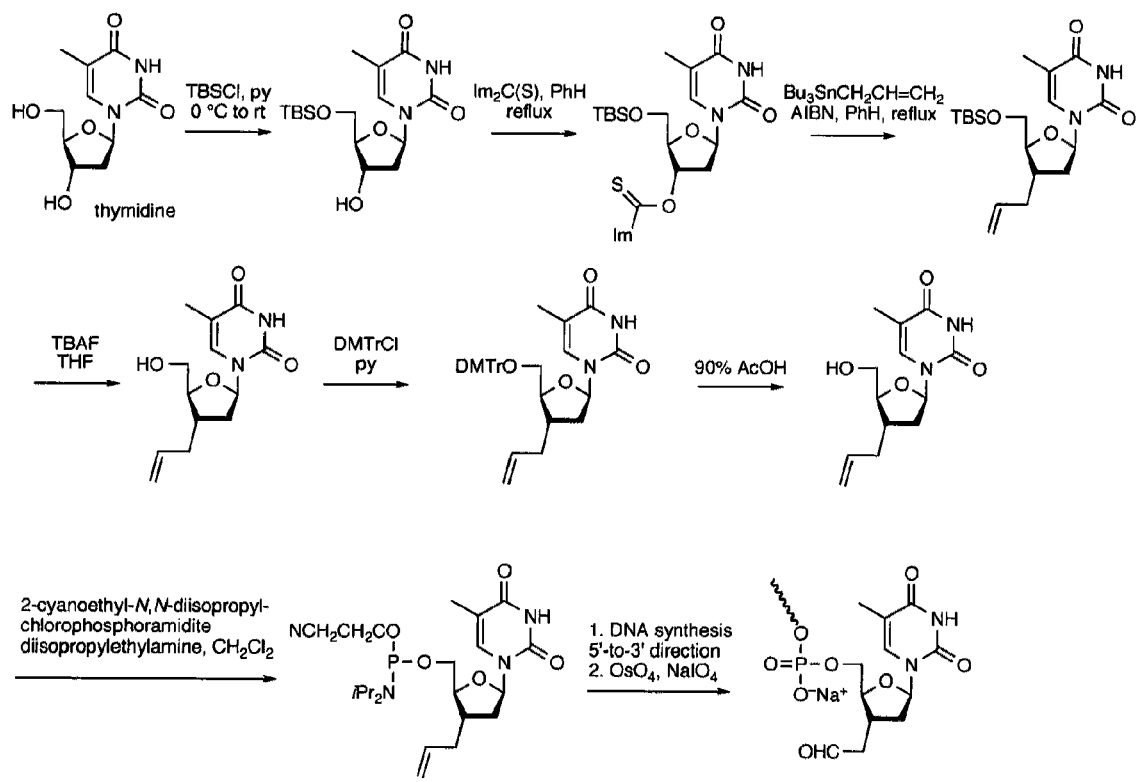
FIG. 3. Preparation of DNA fragments terminated with 3'-$CH_2CHO$ unit for thymidine. Key references for the steps can be found in [Chu89][Zha01][Goo92] For literature, DNA synthesis is done in the unconventional 5'->3' direction [Bog99].

When the target is a DNA molecule, this approach offers the opportunity to assemble a fully complementary composite from, in principle, an unlimited number fragments. The DNA-TACS that joins two fragments is shown in FIG. 2 (above). Imine formation has an equilibrium constant that is typically 1 micromolar. The imine formation is therefore dynamic, and easily reversible. Once equilibrium is achieved, if it is desired, the imine can be reduced with sodium cyanoborohydride at neutral pH to generate the corresponding secondary amine (FIG. 3). Alternatively, the complex can be denatured, the 5'-fragment lost, and the extended primer captured using the free 5'-amino group.

The instant disclosure teaches about the lengths of the fragments. When attempting to model the origin of life, very short fragments are used; Lynn and his coworkers disclosed fragments that are three nucleotides in length. These are too short for the instant invention, as the assembly of two fragments three nucleotides in length (a 3+3) composite does not generate a product, even, with the imine linker formed, that binds to the preselected template with sufficient affinity to support downstream processing.

In the example, the goal is to create a downstream polymerization reaction only when the fully correct template is present. For various applications, including the detection of single nucleotide polymorphisms, the user would prefer not to have the downstream processing if the template is not present, but a different molecule that is one nucleotide different is present. Short fragments (6-15 nucleotides, with the optimal length depending on the temperature where the downstream processing enzyme will work) are preferred, as a single mismatch in a short fragment has a larger impact by lowering the hybridization melting temperature than a single mismatch in a longer fragment.

The 5'-fragment cannot, of course, be elongated by a polymerase (which, throughout this disclosure, we will consider to include reverse transcriptases), as it has a CH$_2$CHO instead of the elongatable 3'-OH group. Thus, even a rather long oligonucleotides can be used as the 5'-fragment. The 3'-fragment can be very short, if the 5'-fragment is long, as a long 3'-fragment is not required to permit the long 5'-fragment to bind.

Of course, as is well known in the art, fragments that are rich in G and C hybridize more tightly than fragments rich in T (when the partner is A) or A. Diaminopurine, as an analog of A, can be used to replace A to obtain tighter binding.

For this application for this example, the most preferable fragments are sufficiently short that they do not bind to the preselected template at the temperature to an extent sufficient to be elongated by the preselected polymerase. At the same time, the combined length of the two fragments must be sufficient to ensure that the composite binds to the template at the preselected temperature, where consideration is given to the possibility that the unnatural imine linker may destabilize duplex formation.

Further, the position of the imine in the composite may be significant for a given application, if the phosphate at the position that is replaced (in this case) by an imine in the composite is at a position that is a binding/recognition site for the polymerase. This consideration is especially important if we chose, as our strategy, to make the 5'-amino fragment very short.

A final consideration is the specificity that is desired. For example, in probing the human genome for a single sequence, a 16mer is (on average) unique. This suggests that a composite assembled in an 8+8 reaction (or, alternatively, a 9+7 reaction), where the numbers indicate the length of the 5'-fragment and the 3'-fragment respectively, is a composite that will bind (on average) to only a single sequence in the human genome.

As a control, the ability of the 3'-fragment 8mer to serve as a primer is used as a control. The dNTPs (100 µM each, dA, dT, dG, dC), where a label is introduced as alpha $^{32}$P-dCTP is presented, with Therminator (New England Biolabs) or murine maloney virus reverse transcriptases as the polymerases (for detecting DNA and RNA, respectively, although the reverse transcriptase also copies DNA) serving in the downstream processing reaction. If the preselected target sequence is present, the 3'-fragment serves as a primer, leading to the synthesis of labeled DNA from the region of the template downstream from the place on the template where the 3'-fragment binds. The generation of this labeled product demonstrates that the template is present, but not if the molecule present differs in sequence from the sequence of the preselected template at one or more nucleotide sites.

This disclosure teaches the importance of the dynamic equilibrium nature of the assembly of the composite, as it permits the assembly of a composite that is the thermodynamically most stable. This is the fragment that is fully complementary to the DNA template. In an assembly experiment under dynamic equilibrium, therefore, thermodynamics determines what fragments are ligated, meaning that the partial mismatch/exact match discrimination ratio is as good as it can be based on the thermodynamics of partial mismatch/ exact match binding constants.

Thus, the dynamic experiment differs from the irreversible template-directed ligation demonstrated by von Kiedrowski, for example [Sie94] [Bag96]. In the latter case, kinetics determines the outcome of the ligation, and partial mismatches are frequently ligated with nearly the same frequency as full matches [Jam99][Jam98][Jam97].

To enable this experiment to become combinatorial, we need to manage the possibility that the fragments themselves, if they contain (for example) A, T, G, and C, will themselves be self complementary. This means that components of a library of sequences may hybridize to themselves.

Figure 7:
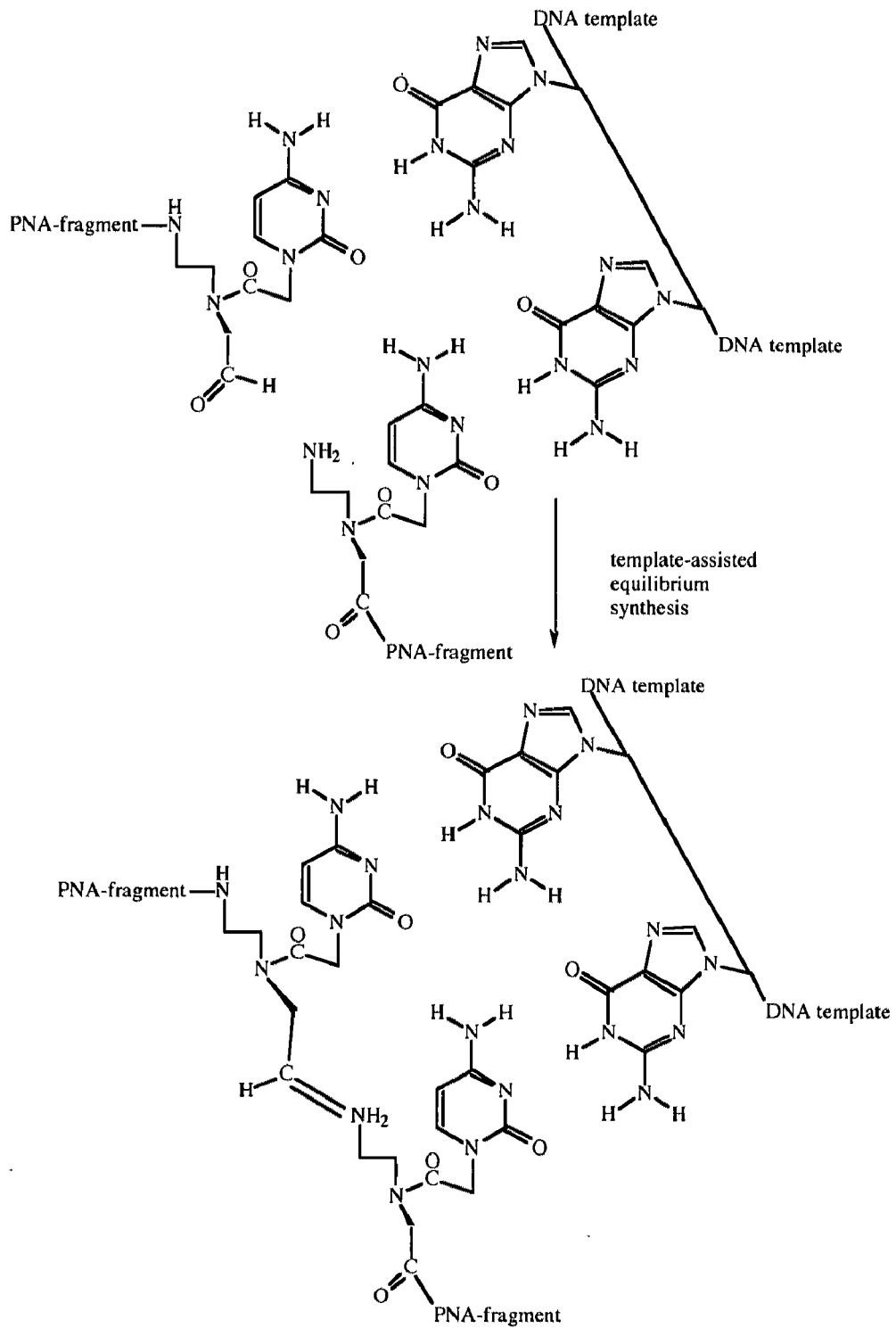
FIG. 7. The details of the imine compositing chemistry using a PNA backbone.

To manage this problem, the instant invention exploits species that are two thirds of hydrogen bonds (FIG. 7). Here, T, C, A, and G analogs are incorporated into the fragments as part of a library, where the analog of T presents just the top two hydrogen bonding elements of T (where "top" means to the major groove side of the nucleobase) positioned to bind to the top two hydrogen bonding elements of A in the target; the analog of A presents just the top two hydrogen bonding elements of A positioned to bind to the top two hydrogen bonding elements of T in the target; the analog of C presents just the top two hydrogen bonding elements of C positioned to bind to the top two hydrogen bonding elements of G in the target; the analog of G presents just the top two hydrogen bonding elements of G positioned to bind to the top two hydrogen bonding elements of C in the target.

The elements of the "two thirds hydrogen bond" fragments are known in the art. Inosine, a well known unit of a well known nucleoside, is one implementation of the G analog, although other heterocycles present the same hydrogen bonding pattern and can be used in the instant invention. 2-Aminopurine, a well known unit of a well known nucleoside, is one implementation of the A analog, although other heterocycles present the same hydrogen bonding pattern and can be used in the instant invention. Likewise, the methylpyridone nucleoside analog has been prepared by McLaughlin and his group [Woo03] and serves as the T analog.

Each of these principles apply with nucleotide fragments build from AEGIS, or on backbone modified analogs of nucleic acids. This is illustrated with polyamide-linked nucleic-acid analogs, also known as peptide nucleic acids, also known as PNAs. PNAs were prepared a decade ago by Nielsen et al. [Nei91]. They were reported to bind to complementary target sequences (DNA or RNA) with a higher affinity than natural oligonucleotides. The binding follows Watson-Crick pairing rules [Nie91].

PNAs cannot be used as primers for DNA polymerases. It was showed, however, in the laboratory of the inventor at the Swiss Federal Institute of Technology, that PNA-DNA chimeras that are terminated with one 2'-deoxynucleoside can serve as primers for some DNA polymerases. Thus, it is known from EP-A 0672 677 that PNA/DNA hybrids with only one 5'-deoxy-5'-aminonucleoside at the carboxyl terminus can be employed as primers if the DNA polymerase from *E. coli* (Klenow fragment) is used for the enzymatic polymerization [Lut97].

A well known feature of PNAs is their propensity to aggregate. This problem becomes more severe as the PNA becomes longer. This is well known in the art. For example, the Applied Biosystems web page, in the form available in August 2001, noted that the "PNA probes do not have to be as long as DNA probes to bind tightly to their target. This is because the PNA backbone is neutral whereas the DNA backbone is negatively charged. As a result, there is no electrostatic repulsion between the PNA probe and its target, making the bond between a PNA probe and its DNA target stronger than between a DNA probe and its DNA target. Therefore, 15-mer PNA probes have roughly the same melting temperatures as 25-mer DNA probes, but retain the specificities of 15-mers. The bottom line is that PNA probes should range in length from 6-20 bases to achieve the best combination of specificity and binding strength." The web site also noted that "Longer probes may tend to aggregate, making purification and characterization difficult. For the instant invention, PNA fragments 4-15 units long is preferred.

The web page also cautions that "Purine-rich sequences tend to aggregate, especially G-rich probes. We recommend adding a solubility enhancer such as "E" to minimize aggregation problems. Nevertheless, the total purine content of the probe should not exceed 85%, and there should not be more than 10 consecutive purines. Furthermore, avoid self-complementary sequences, especially those with more than three Gs in a row." The web site also offered a "Probe Designer [that] calculates the Aggregation Potential of . . . probes based on their hydrogen bonding pattern to ensure successful performance."

One way to avoid the problems of self-aggregation is by having the DNA target itself assemble a PNA. This can be done via a ligation reaction that is essentially irreversible. The instant invention, however, is based on the assembly of PNA fragments via a ligation reaction that is reversible from short, soluble PNA units.

The imine in the compositing chemistry is isosteric with the amide. The carbon is sp2 hybridized, as is the carbonyl carbon of the amide. Therefore, the imine-joined PNA analog has an affinity comparable to that of PNA itself. Further, once formed, the imine can be trapped, using sodium cyanoborohydride. The product is a stable secondary amine. At neutral pH, this linkage is cationic, thus assisting the solubility of the trapped composite. This can be a downstream processing chemistry.

As noted above, a polymerase can be used for downstream processing if the 3'-fragment built from PNA is a PNA-DNA chimera, as in [Lut97] and [Uhl97]. Here, the composite can act as a primer for DNA polymerization. This offers the opportunity to have a template assemble its own primer from a collection of PNA molecules.

To permit the assembly of a library, it is necessary to design the heterocycles carried by the PNA be able to bind to the nucleobases in standard DNA or RNA, but not to each other. This can be done by using the two thirds hydrogen bonding scheme, as discussed above and in FIG. 7.

Requirements for the template-assisted assembly of PNA fragments are fragments of sufficient length to bind with ca. 1 micromolar affinity to a template. These are preferably 4-6 units long, although as few as 3 units and as many as 10 can be used as a part of the instant invention.

Alternative reversible ligation reactions can be considered as alternatives to imine formation. For example, the condensation of an aldehyde with a thiol on the other ligand fragment can generate a thiohemiacetal. Two thiols can join the fragments as a disulfide.

In the method of the instant invention, the target is a DNA, RNA, or PNA molecule having a defined sequence, the fragments are short PNA molecules, or PNA-DNA or PNA-RNA chimeras, that are complementary to consecutive, adjoining, segments of the target, compositing chemistry is the formation of an imine between an aldehyde of one fragment and an amine of the second.

The invention extends to the PNA derivatives terminated by a single 2'-deoxyribonucleoside, as disclosed in [Uhl100]. This can serve as a primer for the DNA-polymerase mediated copying of DNA, or reverse-transcriptase-mediated copying of RNA. Thus, the invention provides methods for primer extension of PNA-DNA chimera from template nucleic acids using polymerases, nucleotide 5'-triphosphates, and primer extension reagents. Structural requirements of the chimera for primer extension include 5 to 15 contiguous PNA monomer units, 3 or more contiguous nucleotides, and a 3' hydroxyl terminus. Thus, the method permits the synthesis of DNA complementary to DNA or RNA with the primer necessary for such synthesis being generated in situ by assembly of PNA fragments exploiting an aldehyde functionality.

EXAMPLES

Example 1

Materials and Methods

Synthesis of 3'-terminal fragments having a 5'-deoxy-5'-aminonucleoside

The 3'-terminal fragments, each carrying a 5'-deoxy-5'-amino nucleoside, were prepared by standard solid phase synthesis using an Expedite 8900 DNA synthesizer according to standard protocols. Phosphoramidites, including the 5'-amino nucleoside analog where the 5'-amino group was protected as a 5'-monomethoxytrityl ether, were purchased from Glen Research. The final detritylation of the protected amine was done with 2% dichloroacetic acid for 15 min. The product was purified by HPLC after the 5'-monomethoxytrityl group was removed.

Synthesis of 5'-terminal fragments having a 3'-deoxy-2'-carbonylmethylene unit

The 5'-terminal fragments (8, 10, i) were obtained using standard DNA synthesis done in the unconventional 5'->3' direction (ii) on an Expedite 8900 DNA synthesizer. FIG. 2 shows the scheme for their preparation.

3'-Deoxy-3'-C-allyl-5'-O-[cyanoethyl-(N,N-diisopropylamino)phosphinyl]thymidine (5), the building block for the syntheses of the 3'-terminal aldehydes unit This compound was prepared using the procedure described by Lynn and his coworkers (10), adapted as described below. To a mixture of 3'-deoxy-3'-C-allylthymidine (4, 190 mg, 0.71 mmol, Supplemental) and diisopropylethylamine (204 µL, 1.17 mmol) in $CH_2Cl_2$ (7 mL) was added 2-cyanoethyl-diisopropylchlorophosphoramidite (239 mg, 1.07 mmol) at 0° C. The mixture was warmed to room temperature and stirred for 1 h. The mixture was diluted with $CHCl_3$, and the organic phase was washed with sat. $NaHCO_3$ and brine, dried over $Na_2SO_4$ and evaporated. The residue was purified by column chromatography ($SiO_2$, 40-60% AcOEt in hexane with 0.5% $Et_3N$ to give 4 (247 mg, 75%) as a pale brown solid: $^1$H-NMR (300 MHz, $CDCl_3$) δ 8.75 (br s, 1H), 7.75 (d, 1H, J=1.2), 7.56 (d, 1H, J=1.2), 6.11 (m, 1H), 5.75 (m, 1H), 5.07 (m, 2H), 4.04-3.76 (m, 5H), 3.63 (m, 2H), 2.64 (m, 2H), 2.42-2.09 (m, 5H), 1.95 (d, 1.5H, J=1.2), 1.94 (d, 1.5H, J=1.2), 1.20 (m, 12H); $^{13}$C-NMR (75 MHz, $CDCl_3$) δ 163.86, 150.31, 136.04, 135.70, 135.21, 135.12, 117.34, 117.28, 110.24, 110.18, 85.17, 84.92. 84.83, 84.49, 64.23, 64.01, 62.74, 62.54, 58.80, 58.47, 58.20, 43.29, 43.20, 43.13, 43.04, 38.74, 38.47, 37.77, 37.05, 36.52, 36.26, 24.65, 24.55, 20.40, 12.52, 12.38; $^{31}$P-NMR (121 MHz, $CDCl_3$) δ 149.43 (s), 149.02 (s); HRMS (FAB) calcd for $C_{22}H_{36}N_4O_5P$ 467.2423, found 467.2433 (MH$^+$).

Polymerase Extension

Polymerases

Bst, Deep Vent$_R$®, Deep Vent$_R$® (exo$^-$), Taq, DNA polymerase I Large (Klenow) Fragment, Klenow Fragment (exo$^-$), 9°N$_m$™ and Therminator™ polymerases were purchased from New England Biolabs (Beverly, Mass.). M-MuLVRT, AMVRT and Tth polymerases were purchased from Promega (Madison, Wis.). Pfu and Pfu (exo$^-$) polymerases were purchased from Stratagene (La Jolla, Calif.). Buffers used in these experiments were supplied by the manufacturer. Bst, Taq, Vent, Deep Vent, 9° N and Therminator use Thermopol Buffer (1x): 20 mM Tris-HCl (pH 8.8, 25° C.), 10 mM KCl, 10 mM $(NH_4)_2SO_4$, 2 mM $MgSO_4$, 0.1% Triton X-100. Klenow and Klenow exo$^-$ use NEB 2 (1x): 50 mM NaCl, 10 mM Tris-HCl, 10 mM $MgCl_2$, 1 mM dithiothreitol (DTT) (pH 7.9, 25° C.). AMVRT uses buffer (1x): 50 mM Tris-HCl (pH 8.3, 25° C.), 50 mM KCl, 10 mM Mg $Cl_2$, 0.5 mM spermidine and 10 mM DTT. M-MuLVRT uses buffer (1x): 50 mM Tris-HCl (pH 8.3, 25° C.), 75 mM KCl, 3 mM $MgCl_2$, and 10 mM DTT.

Primer Extension Assays

For primer extension assays (10 µL reaction volume) formyl 8-mer (20 pmol) and/or amine 8-mer or 6-mer (20 pmol) and DNA Template (30 pmol) were annealed by incubation at 96° C. for 5 min and allowed to cool to room temperature over 1 hour. Polymerases were used at 2 U per reaction with the exception of AMVRT (10 U/reaction) and M-MuLVRT (200 U/reaction). Manufacturer's supplied buffer and polymerase were added to primer template complex and incubated at appropriate temperature for 30 sec. Each reaction was initiated by adding dNTP solution (1 µL, 100 µM each; dATP, dTTP, dGTP and dCTP) and 33 nM $α^{32}$P-dCTP) to the reaction mixture (9 µL) and were incubated at appropriate temperatures for 2 min. Reactions were quenched by the addition of 5 µL PAGE loading/quench buffer (98% formamide, 10 mM EDTA, 1 mg/mL xylene cyanol FF and 1 mg/mL bromophenol blue). Samples (1 µL) were resolved on denaturing polyacrylamide gels (7 M Urea and 20% 40:1 acrylamide:bisacrylamide) and analyzed with a Molecular Imager FX system (BioRad, Hercules, Calif.).

Primer Extension Using Alternative Templates

Oligonucleotides (Table 1) were synthesized and PAGE purified from Integrated DNA Technologies (Coralville, Iowa). These various oligonucleotides have one nucleotide mismatch at different sites where the formyl and amine primers anneal. Modified nucleotides are numbered based on their location in the template. The assays were run as described above however the standard template in the reaction mixture was substituted with an alternative template. These primer extensions were run with the formyl 8-mer, amine 8-mer, and M-MuLVRT at 35° C. Additional primer extensions were run with the formyl 8-mer, amine 6-mer, and 9° N at 70° C. Samples (1 µL) were resolved on a 20% denaturing PAGE and analyzed with a Molecular Imager FX system.

Methoxylamine Treatment

After completion of the primer extensions assays an aliquot was treated with methoxylamine hydrochloride (1M, Sigma) and incubated at 94° C. for 1 hour. The sample was then resolved on a 20% denaturing PAGE and analyzed with a Molecular Imager FX system.

The basic architecture in assembles two fragments: (1) a 3'-fragment, which has an elongatable 3'-OH group and a 5'-amino group able to form an imine, and (2) a 5'-fragment, where a $CH_2$—CHO unit replaces its 3'-OH, permitting it to form an imine with the 3'-fragment. The first are readily available from commercial supply houses. The second, having a $CH_2$CHO unit at its 3'-end, was synthesized from the appropriate precursor, which in turn was prepared by the scheme shown in FIG. 2.

Figure 1:
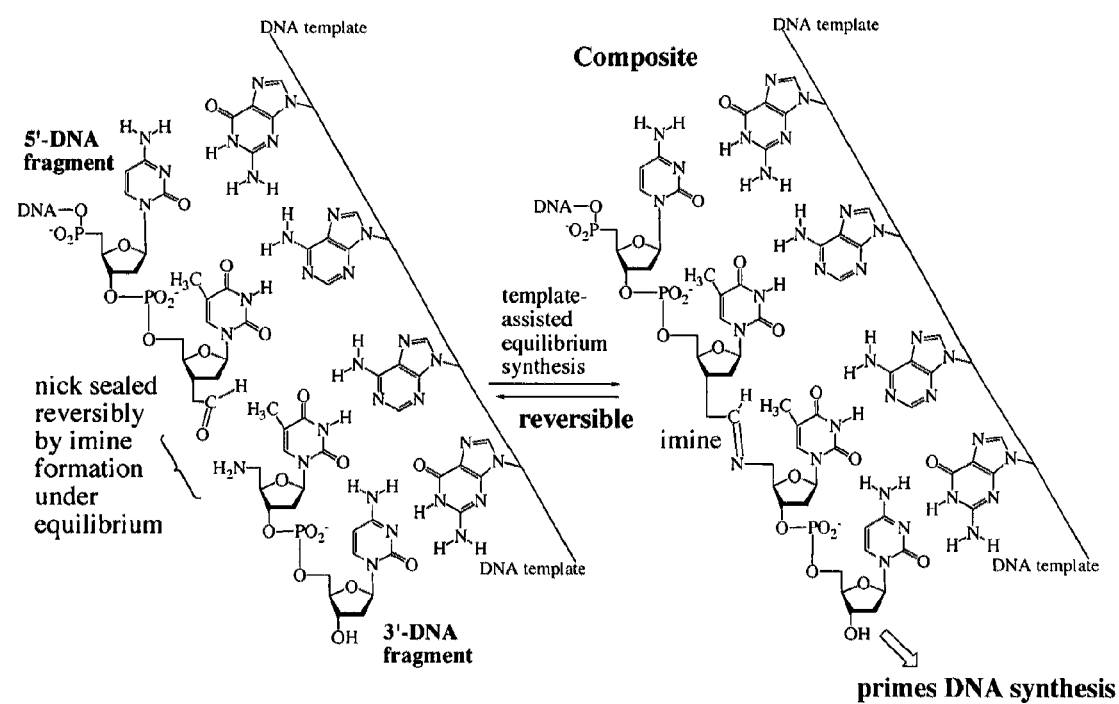
FIG. 1. DNA fragments terminated with 3'-$CH_2$CHO (on the 5'-DNA fragment) and 5'-$CH_2$—$NH_2$ (on the 3'-DNA fragment) will reversibly form a composite, joined via an imine linker under conditions of dynamic equilibrium. The reversibility ensures that the tightest binding complement perfectly matched to the template is formed. This composite will be long enough to bind tightly enough to prime the synthesis of DNA using a DNA polymerase. The 5'-end of the 5'-fragment can be an HO-unit, phosphate, 5'-labelled phosphate, or any other species, as this end does not enter into any chemical reactions. The fragments must have at least four nucleotide units, making the smallest integers of m and n in the claims be 2. More preferably, however, the fragments have at least five nucleotide units, making the smallest integers of m and n (which need not be identical) in the claims be 3.

For architecture outlined in FIG. 1 to be implemented, polymerases must be found that do not prime from a 3'-terminal fragment by itself, but do prime from it in the presence of the 5'-terminal fragment. Naively, we expected that short DNA molecules would generally not prime if the temperature of the polymerase incubation were significantly higher than the melting temperature for the short primer-template duplex. Examination of a variety of polymerases showed that this was not the case with all polymerases (FIG. 3). Thus, many polymerases were able to use short 8-mer DNA molecules as primers at temperatures above the nominal melting temperature of the DNA duplexes. Only murine MuLV reverse transcriptase rejected the 8-mer primer entirely, although Pfu exo$^+$ generated only traces of full length product at 55° C., and no detectable product at higher temperatures.

For the remaining polymerases, significant amounts of priming were observed at temperatures above the nominal melting temperatures. In most cases, the amount of priming decreased as the temperature was raised. With various Klenow fragments, whose thermal instability prevented incubation at high temperature, the extent of full length product produced tracked the activity of the polymerase itself.

This screen allowed M-MuLVRT and Pfu polymerase to be viewed as lead polymerases to implement the desired architecture. These did not efficiently use the 8-mer 3'-fragment by itself as a primer. For them to used, however, the 8-mer 3'-fragment bearing a 5'-amino group must be accepted by the polymerases as a primer when it forms transiently an imine complex with an 8-mer that bound immediately upstream.

Figure 4:
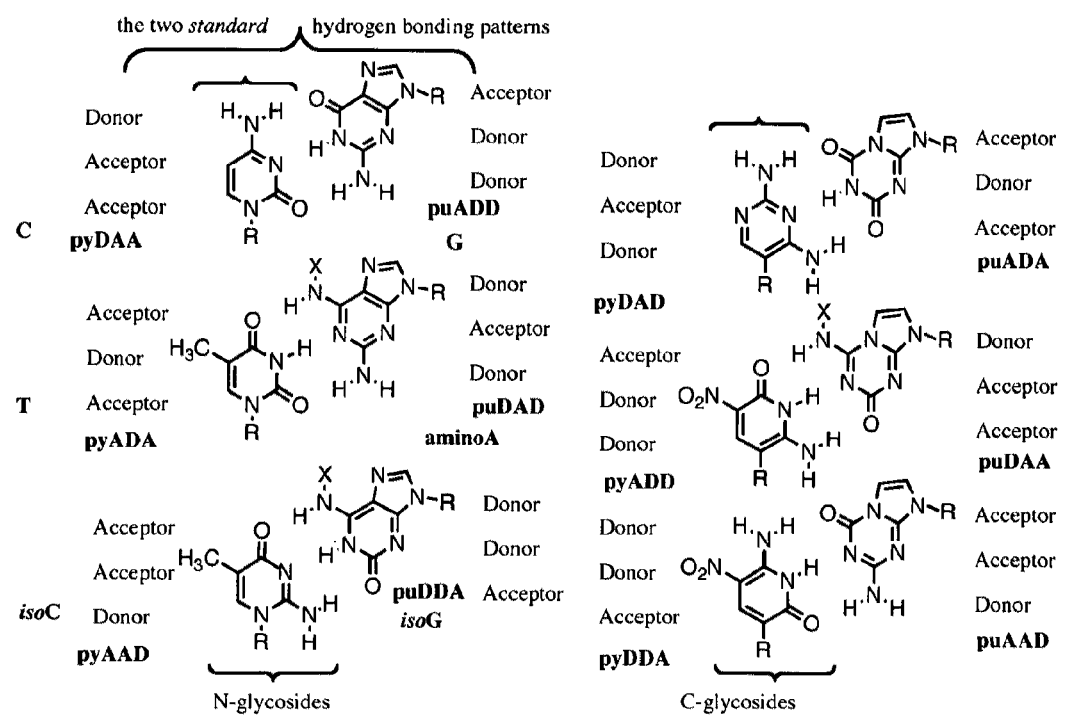
FIG. 4. Twelve possible nucleobases in a DNA- or RNA-based "alphabet" that can form specific base pairs within the constraints of the Watson-Crick base pair geometry. Pyrimidine base analogs are designated by "py", purine by "pu". The upper case letters following the designation indicate the hydrogen bonding pattern of acceptor (A) and donor (D) groups. Thus, the standard nucleobase cytosine is pyDAA, guanosine is puADD (for example). X indicates sites where functional groups might be appended.

The data collected in FIG. 4 shows that both Pfu and M-MuLVRT were able to extend an 8-mer fragment bearing a 5'-amino group, but only in the presence of a second fragment carrying a 3'-CH$_2$CHO unit complementary to the sequence immediately adjacent in the DNA template. Two types of evidence were collected that suggested that the imine was actually being formed. First, it was possible to detect the imine intermediate by the presence of a band at the position on the gel where a 19-mer would be expected to run (see higher bands in FIG. 4 and following). The fact that this band was the imine was demonstrated by showing that its intensity was reduced when the mixture was incubated with methoxylamine prior to gel analysis; the methoxylamine should disrupt the imine complex by itself forming an imine with the aldehyde group.

Further, in several test cases, the imine presumed to be formed transiently was reduced in situ with sodium cyanoborohydride, a procedure that was expected to join the two fragments via a stable secondary amine linker. Mass spectrometry identified the expected amine product (C$_{156}$H$_{202}$N$_{54}$O$_{90}$P$_{14}$, calculated mass: 4704.9216. observed: 4707.87, 2355.51, and 1571.24 assigned as the monoanion, dianion, and trianion respectively).

Figure 5:
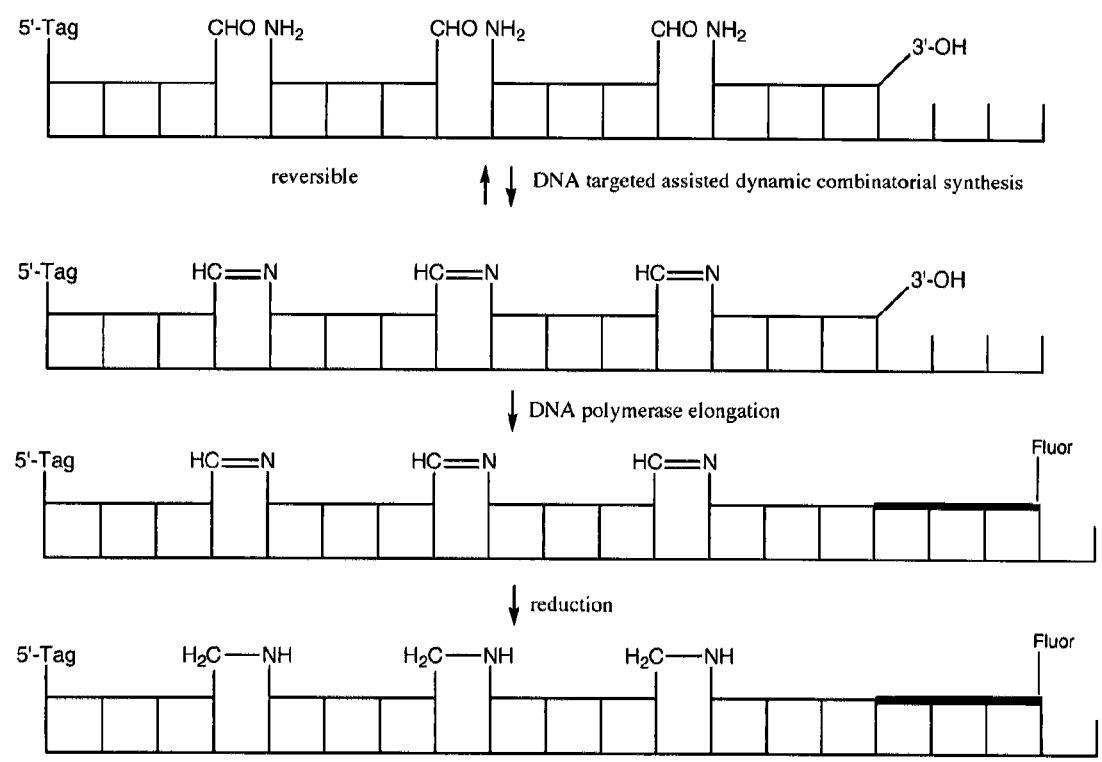
FIG. 5. Schematic showing the assembly of four fragments after the instant invention, where a DNA sequence is the template.

With polymerases in hand that extended only composite primers formed in situ under conditions of dynamic equilibrium, we asked whether the dynamically assembled primer could be used to discriminate against single nucleotide mismatches. FIG. 5 collects data obtained with murine MuLVRT that shows it does. Here, the primer extension assays examined with DNA 38-mer templates containing single mismatches at various positions throughout the binding region (see Table 1 for details of mismatches).

Perhaps not surprisingly, a mismatch at the 3'-end of the composite primer resulted in no detectable elongation. Mismatches at every other site resulted in decreased elongation, with the overall pattern roughly consistent with expectations based on general concepts of the impact of mismatches on duplex stability. Thus, mismatches at the 5'-end of the 5'-fragment had the smallest (but still detectable) impact on composite primer extension, while mismatches in the middle of the fragments had the largest impact. Purine-purine and pyrimidine-pyrimidine mismatches generally diminish elongation more than purine-pyrimidine mismatches. The only clear exception to this generalization is at Site 20, on the 5'-end of the imine junction. Nevertheless, mismatches at the imine junction uniformly diminished the efficiency of priming by the composite; a priori, this outcome was not obvious, as mismatches could conceivably have been favored given the distortion of the geometry of the backbone caused by the imine.

Figure 6:
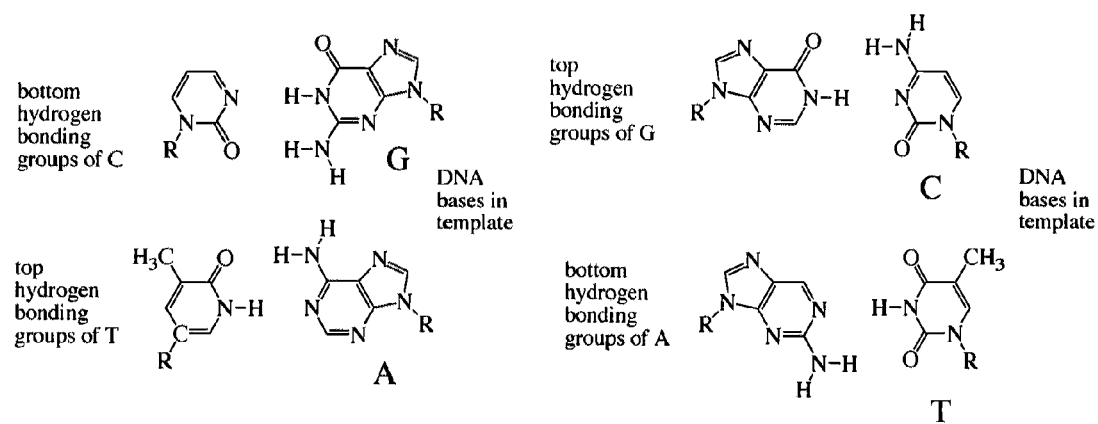
FIG. 6. By using base pairs joined by two hydrogen bonds, a series of nucleobases can be designed, to be placed on a PNA or DNA backbone, that will bind to natural G, A, C, and T (by two hydrogen bonds), but not to each other (by more than one hydrogen bond). This allows the sequences in the fragments to be orthogonal to other fragment sequences.

These results demonstrate the use of M-MuLVRT as a part of an 8+8 architecture where one could discriminate between single mismatches. With this proof of concept in hand, we asked whether shorter primer fragments might allow discrimination to be more complete, or allow other polymerases to be used, especially thermostable polymerases that allowed a wider range of temperatures to be exploited to obtain higher levels of mismatch discrimination. FIG. 6 shows the results when the same DNA 38-mer template was presented with a 6-mer (instead of an 8-mer) as the 3'-fragment. Among the thermostable polymerases at high temperature, only Therminator and Bst generated detectable amounts of full length product using the 3'-terminal 6-mer fragment alone, and these only at the lower temperatures examined. Klenow fragment again primed efficiently from the 6-mer by itself, again presumably because the lower incubation temperature required by this polymerase permitted less stable duplexes to form.

The identification of conditions where many thermostable polymerases did not elongate a 6-mer primer terminated with a 5'-amino group allowed us to use several of these to selectively elongate a composite primer. FIG. 7 shows a collection of data. Virtually all of the polymerases primed from the 8+6 composite to yield full length product. As before, some of the imine composite could be recovered on the gel if electrophoresis was done without substantial dilution of the mixture.

Figure 8:
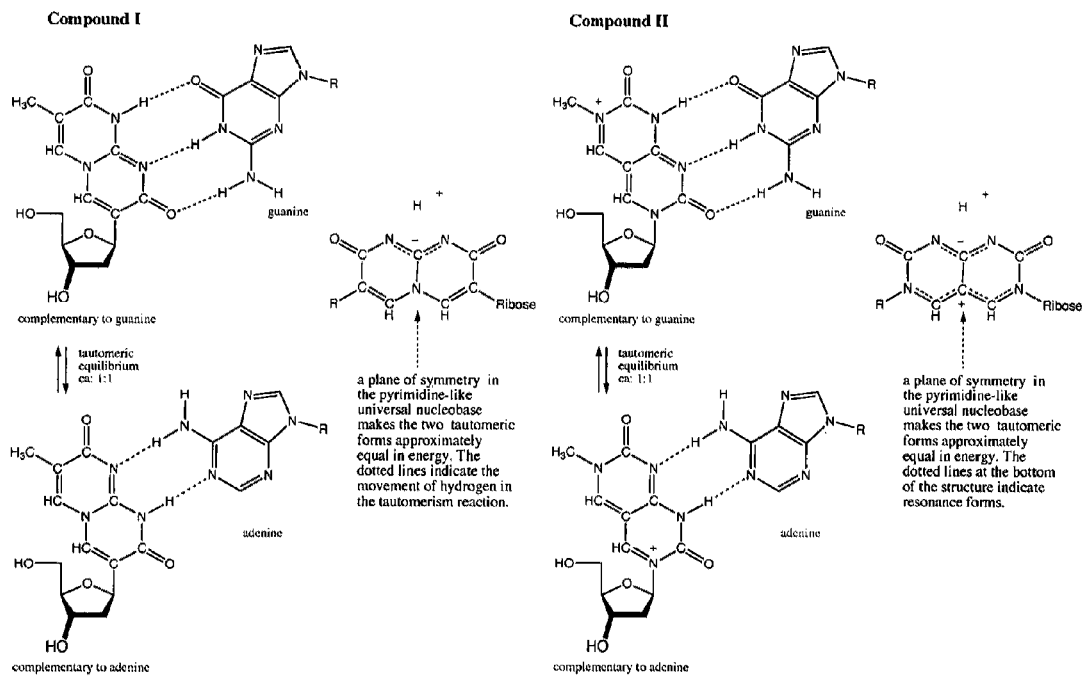
FIG. 8. Pyrimidine-like universal nucleobases that will Watson-Crick bind to both A and G in the preselected template. As described by [Uhl97] and [Lut97], the 3'-nucleoside unit can be attached as either the 5'-ester (where it is derived from a standard nucleoside) or 5'-amide, where it is derived from a 5'-deoxy-5'-aminonucleoside. The latter, having increased stability, is preferred.

From this set of data, the 9° N polymerase was selected as a candidate for more detailed study to determine whether assay conditions could be obtained with a thermostable polymerase that would allow for complete mismatch discrimination. The results in FIG. 8 show that at 70° C., the 9° N DNA polymerase efficiently elongated the 8+6 composite, but did not elongate any composite primers containing the mismatches examined in the 6-mer fragment to any detectable extent. Further, the polymerase did not elongate composite primers containing most of the selected mismatches in the 8-mer 5'-fragment. The notable exceptions were mismatches at the 5'-end of the 5'-fragment (where a TT mismatch still prevented composite primer elongation) and at the junction at the 3'-end of the 5'-fragment (but even here, TT and TC mismatches disrupted elongation).

The DNA fragments to be used in this work come in two types: 5'-amino terminated and 3'-CH$_2$CHO terminated. The first are obtained from commercial supply houses, where the 5'-terminal amino group is introduced in the last step of the synthesis. The 3'-terminated fragments are known in the art ([Chu89][Zha01][Goo92]); DNA synthesis is done in the unconventional 5'→3' direction [Bog99]. FIG. 4 shows the scheme for their preparation.

Tables

TABLE 1

Oligonucleotides

| Name | Sequence (5' to 3')[a] | Modification | |
|---|---|---|---|
| T1 | CGGTTTATGAGGTTTGGGA \| AAAGTGTAGATGGTGATGT | None | SEQ ID NO 1 |
| T2 | CGGTTTATGAGA̲TTTGGGA \| AAAGTGTAGATGGTGATGT | 12G to A | SEQ ID NO 2 |
| T3 | CGGTTTATGAGT̲TTTGGGA \| AAAGTGTAGATGGTGATGT | 12G to T | SEQ ID NO 3 |

TABLE 1-continued

Oligonucleotides

| Name | Sequence (5' to 3')[a] | Modification | |
|---|---|---|---|
| T4  | CGGTTTATGAGCTTTGGGA \| AAAGTGTAGATGGTGATGT | 12G to C | SEQ ID NO 4 |
| T5  | CGGTTTATGAGGTTCGGGA \| AAAGTGTAGATGGTGATGT | 15T to C | SEQ ID NO 5 |
| T6  | CGGTTTATGAGGTTGGGGA \| AAAGTGTAGATGGTGATGT | 15T to G | SEQ ID NO 6 |
| T7  | CGGTTTATGAGGTTAGGGA \| AAAGTGTAGATGGTGATGT | 15T to A | SEQ ID NO 7 |
| T8  | CGGTTTATGAGGTTTGGGG \| AAAGTGTAGATGGTGATGT | 19A to G | SEQ ID NO 8 |
| T9  | CGGTTTATGAGGTTTGGGC \| AAAGTGTAGATGGTGATGT | 19A to C | SEQ ID NO 9 |
| T10 | CGGTTTATGAGGTTTGGGT \| AAAGTGTAGATGGTGATGT | 19A to T | SEQ ID NO 10 |
| T11 | CGGTTTATGAGGTTTGGGA \| GAAGTGTAGATGGTGATGT | 20A to G | SEQ ID NO 11 |
| T12 | CGGTTTATGAGGTTTGGGA \| CAAGTGTAGATGGTGATGT | 20A to C | SEQ ID NO 12 |
| T13 | CGGTTTATGAGGTTTGGGA \| TAAGTGTAGATGGTGATGT | 20A to T | SEQ ID NO 13 |
| T14 | CGGTTTATGAGGTTTGGGA \| AAAATGTAGATGGTGATGT | 23G to A | SEQ ID NO 14 |
| T15 | CGGTTTATGAGGTTTGGGA \| AAATTGTAGATGGTGATGT | 23G to T | SEQ ID NO 15 |
| T16 | CGGTTTATGAGGTTTGGGA \| AAACTGTAGATGGTGATGT | 23G to C | SEQ ID NO 16 |
| T17 | CGGTTTATGAGGTTTGGGA \| AAAGTGTGGATGGTGATGT | 27A to G | SEQ ID NO 17 |
| T18 | CGGTTTATGAGGTTTGGGA \| AAAGTGTCGATGGTGATGT | 27A to C | SEQ ID NO 18 |
| T19 | CGGTTTATGAGGTTTGGGA \| AAAGTGTTGATGGTGATGT | 27A to T | SEQ ID NO 19 |
| T20 | CGGTTTATGAGGTTTGAGA \| AAAGTGTAGATGGTGATGT | 17G to A | SEQ ID NO 20 |
| T21 | CGGTTTATGAGGTTTGTGA \| AAAGTGTAGATGGTGATGT | 17G to T | SEQ ID NO 21 |
| T22 | CGGTTTATGAGGTTTGCGA \| AAAGTGTAGATGGTGATGT | 17G to C | SEQ ID NO 22 |
| Region copied | 3'-terminal 5'-terminal | | |
|  | 5'-amino    3'-formyl | | |
|  | binding site binding site | | |

[a]Bold indicates the portions of the template that are matched by the fragments. The vertical line | indicates the junction between the fragment binding sites. The 5'-amino 3'-terminal fragment binds to the left of the vertical lines; template binding sites for 8-mers and 6-mers are shown.
The top template (T1) is perfectly matched to the fragments. The remaining templates have a single mismatch (underlined) for either the 3-terminal 5'-amino fragment (T2 through T10, and T20 through T22) or the 5'-terminal 3'-formyl fragment (T11 through T19). Position numbers are counted from the 5'-end of the template.

TABLE 2

List of oligonucleotide analogs used in this work

| Name | Sequence (3' to 5') |
|---|---|
| 5'-fragment precursor(allyl) | 3'-H$_2$C=CHCH$_2$C-TTTCACAT-5' |
| 5'-fragment precursor(diol) | 3'-HOH$_2$C(HO)HCH$_2$C-TTTCACAT-5' |
| 5'-fragment(aldehyde) | 3'-OHCH$_2$C-TTTCACAT-5' |
| 3'-fragment(NH$_2$, 6mer) | 3'-AACCCT-NH$_2$-5' |
| 3'-fragment(NH$_2$, 8mer) | 3'-CAAACCCT-NH$_2$-5' |

Example 2

Polymerase Extension

The templated assembly of the fragments is done in polymerase buffer (phosphate, lacking buffer amino groups) in the presence of 2'-deoxynucleoside triphosphates and a thermostable polymerase. The Terminator DNA polymerase I, Vent DNA polymerase, and Tth DNA polymerase are preferred.

Example 3

Using RNA as the Template

In this process, reverse transcriptase is used instead of a DNA polymerase, and the reaction conditions are adjusted accordingly. The reverse transcriptases from human immunodeficiency virus, avian myeloblastosis virus (AMV) and moloney murine leukemia virus (M-MuLV) are preferable.

Example 4

Multiple Assembly

DNA-TACS is especially valuable if it can assemble n fragments, each m nucleotides in length to form oligomers that are n×m in length complementary to a template. This is shown schematically in FIG. 6.

To do this requires three types of fragments:

(a) Connector fragments that have both a 5'-amino group and a 3'-CH$_2$—CHO unit. These are preferably 4-15 nucleotide units in length.

(b) A 5'-terminating fragment (in FIG. 6, with a capture tag), that has a 3'-$CH_2$—CHO unit. This is preferably 4-15 nucleotide units in length.

(c) A 3'-terminating fragment, which has a 5'-amino group, and a 3'-OH group. This is preferably 4-15 nucleotide units in length.

Figure 10:
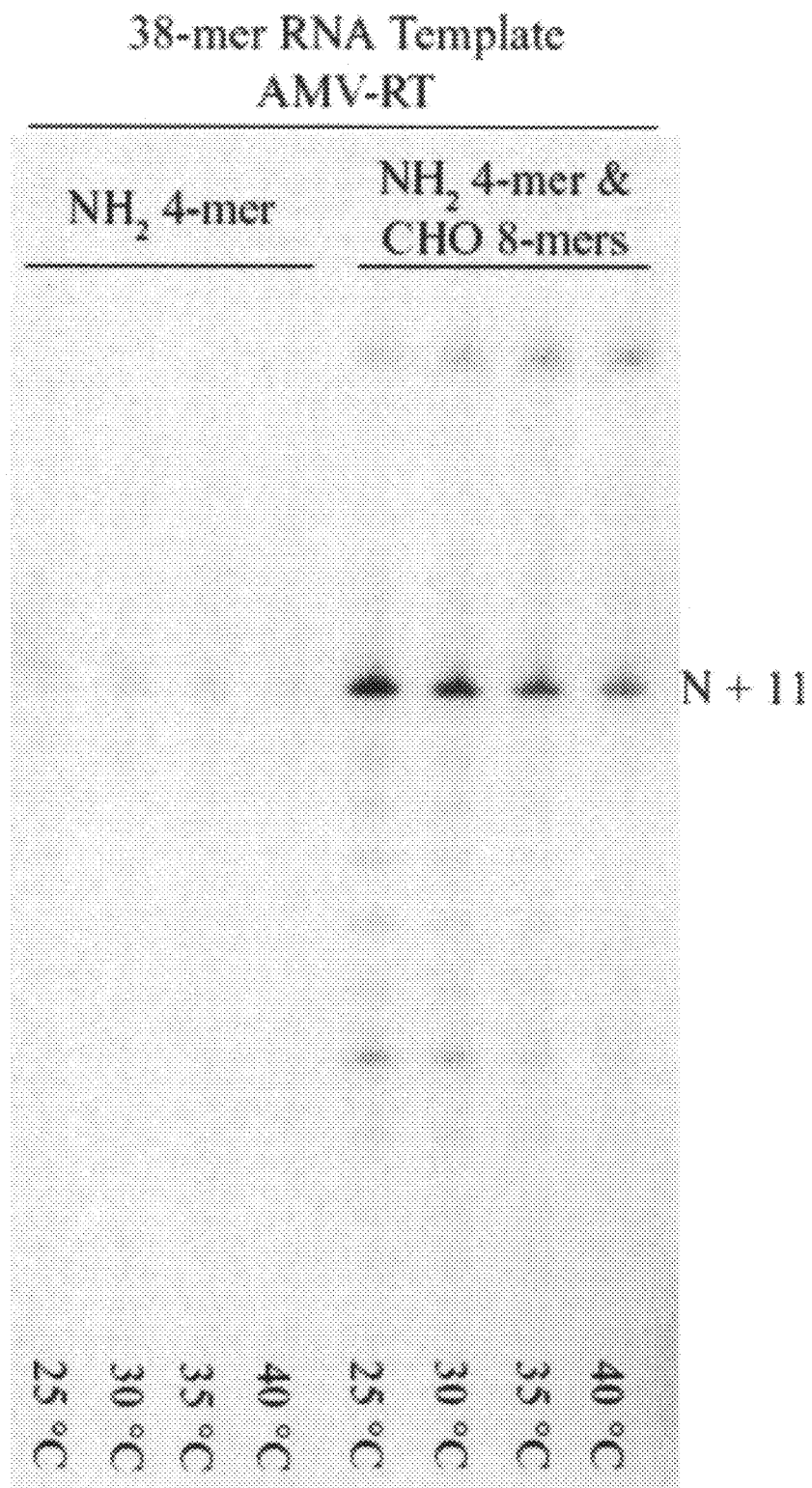
FIG. 10. Extension of a composite primer made from a 5'-fragment that is eight nucleotides long carrying a 3'-$CH_2CHO$ unit, and a 3'-fragment that is a four nucleotides long carrying a 5'-amino group. The left lanes are the controls at the indicated temperatures that have only the 3'-fragment that is a four nucleotides long carrying a 5'-amino group. The right lanes are experiments, at the indicated temperatures, where both the a 5'-fragment that is eight nucleotides long carrying a 3'-$CH_2CHO$ unit and the 3'-fragment that is a four nucleotides long carrying a 5'-amino group. The enzyme is AMV reverse transcriptase.
Figure 11:
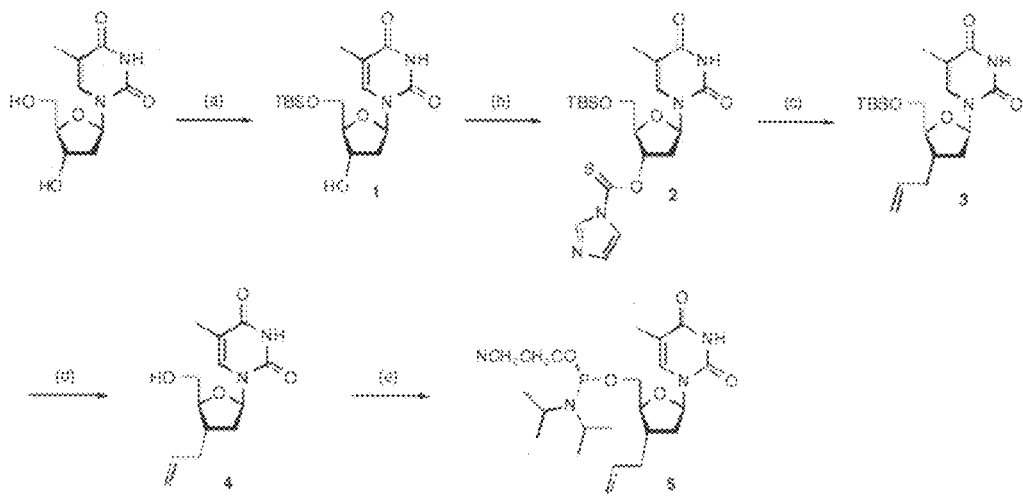
FIG. 11. Synthesis of materials used in Example 1.
Figure 11:
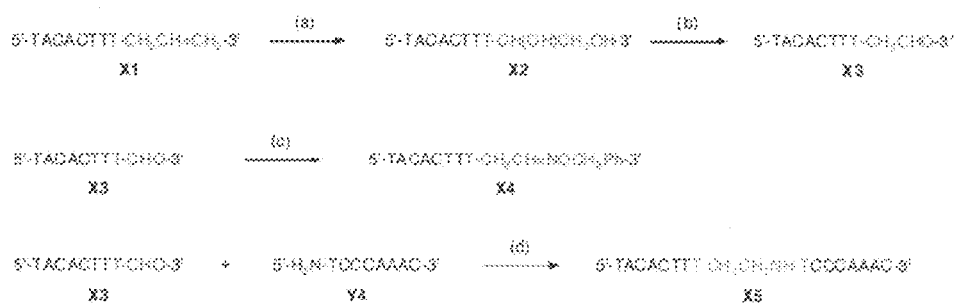
Figure 12:
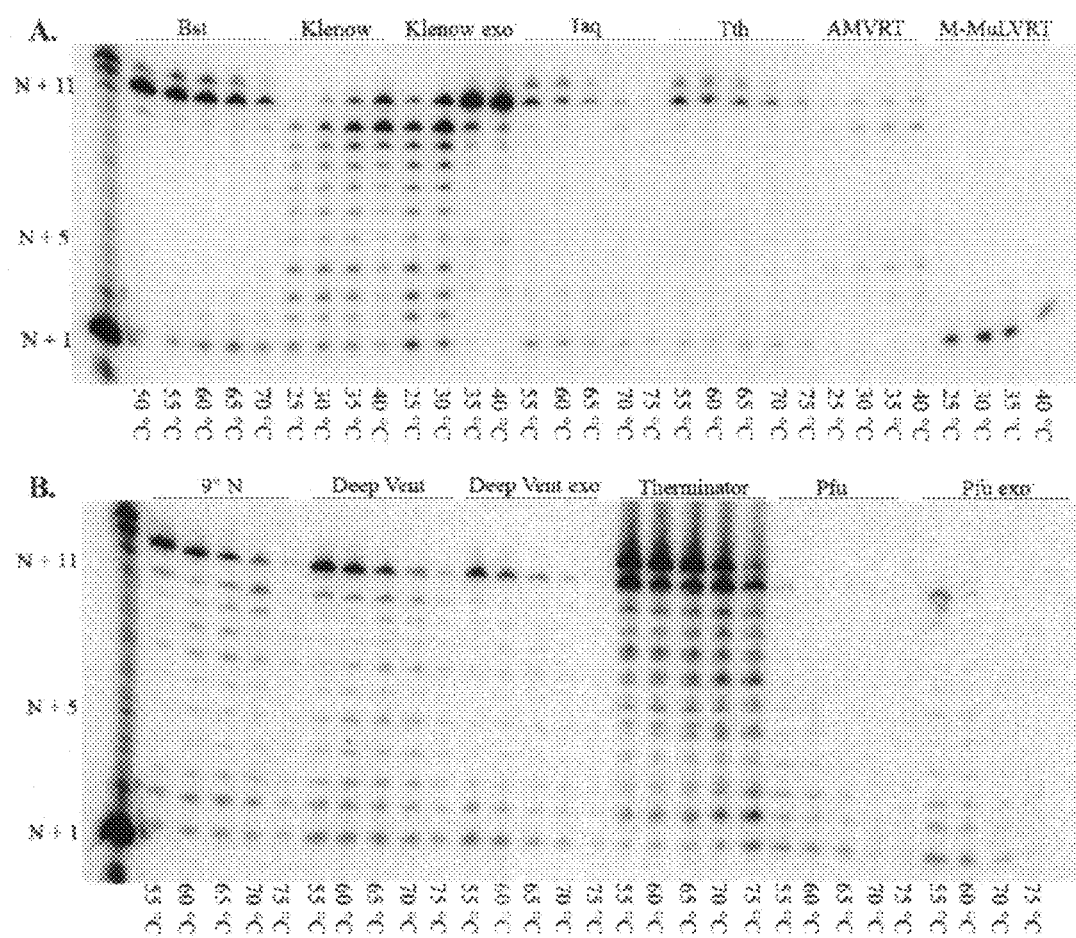
FIG. 12. Extension of the 8-mer primer. See Tables 1 and 2 for the sequences of oligonucleotides used. Final concentrations: dNTPs (100 µM each, for A, T, G, C, with 33 nM alpha $^{32}$P-dCTP) template (30 pmol, 3 µM), and 3'-terminal 8-mer fragment carrying a 5'-amino group (2 µM, 20 pmol). The mixtures containing the indicated polymerase were brought to the indicated temperature for 30 sec and dNTPs were added. The mixtures were incubated at the indicated temperatures for 2 min. Reactions were terminated with quench buffer (5 formamide EDTA, dyes, dilution factor of 33%). An aliquot (1 µl) was loaded on a polyacrylamide gel (20%, 7 M urea) and resolved. Surprisingly, a large number of polymerases extended the 8-mer amine at temperatures well above the melting temperature of the duplex.
Figure 13:
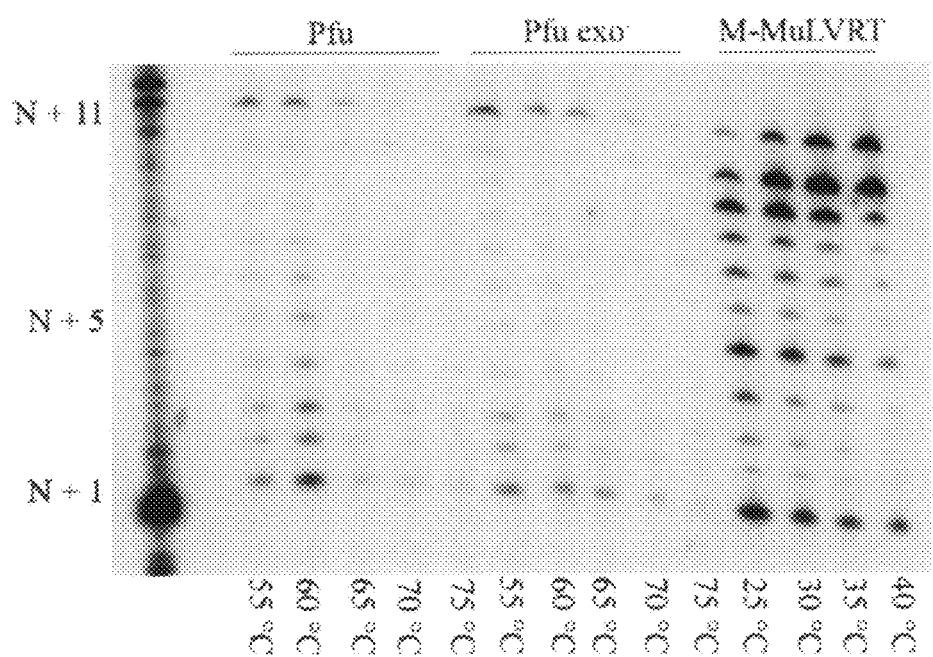
FIG. 13. Primer extension assays using a complementary 3'-terminal 5'-amino-8-mer and 5'-terminal 3'-aldehyde-8-mer with M-MuLVRT, Pfu, and Pfu exo⁻ polymerases, selected based on the data in FIG. 2. Final concentrations: dNTPs (100 µM each, for A, T, G, C, with 33 nM alpha $^{32}$P-dCTP) template (30 pmol, 3 µM), 3'-terminal 8-mer fragment carrying a 5'-amino group (20 pmol, 2 µM), and 5'-terminal 3'-aldehyde-8-mer (20 pmol, 2 µM). The mixtures containing the indicated polymerase were brought to the indicated temperature for 30 sec and dNTPs were added. The mixtures were incubated at the indicated temperatures for 2 min. Reactions were terminated with quench buffer (5 µl, formamide EDTA, dyes, dilution factor of 33%). An aliquot (1 µl) was loaded on a polyacrylamide gel (20%, 7 M urea) and resolved. This experiment identifies M-MuLVRT as a reverse transcriptase suitable for querying biological mixtures for specific DNA molecules using the 8+8 strategy. Addition of the 8-mer 5'-fragment aldehyde also generates substantial amounts of composite primer extension with Pfu polymerase.
Figure 14:
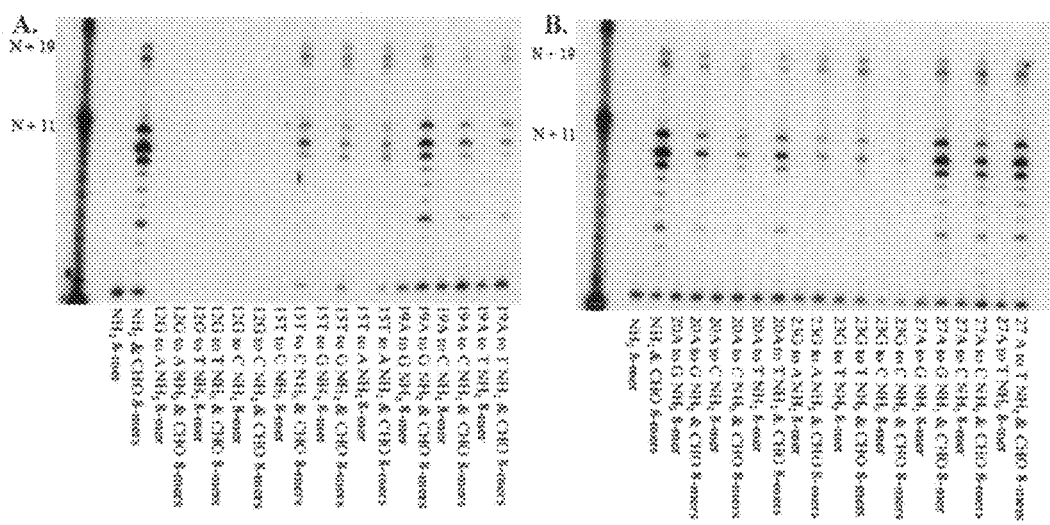
FIG. 14. Mismatch discrimination using M-MuLVRT. PAGE gel (20%) of primer extension assays with mismatched DNA 38-mer templates using M-MuLVRT. Panel A and B contains the mismatches in the site of binding of the 3'-fragment 8-mer and 5'-fragment 8-mer, respectively (see Table 1 for details of mismatches). Final concentrations: dNTPs (100 µM each, for A, T, G, C, with 33 nM alpha $^{32}$P-dCTP) template (30 pmol, 3 µM), 3'-terminal 8-mer fragment carrying a 5'-amino group (20 pmol, 2 µM), and 5'-terminal 3'-aldehyde-8-mer (20 pmol, 2 µM). The reaction mixtures were brought to 35° C. (30 sec) and dNTPs were added. The mixtures were incubated for 2 min at the appropriate temperature. Reactions were terminated with quench buffer (5 µl, formamide EDTA, dyes, dilution factor of 33%). An aliquot (1 µl) was loaded on a polyacrylamide gel (20%, 7 M urea) and resolved. The N+19 band comes from residual imine. The lanes are paired, with, following the amine fragment lacking the formyl, fully matched, one nucleotide mismatched.
Figure 15:
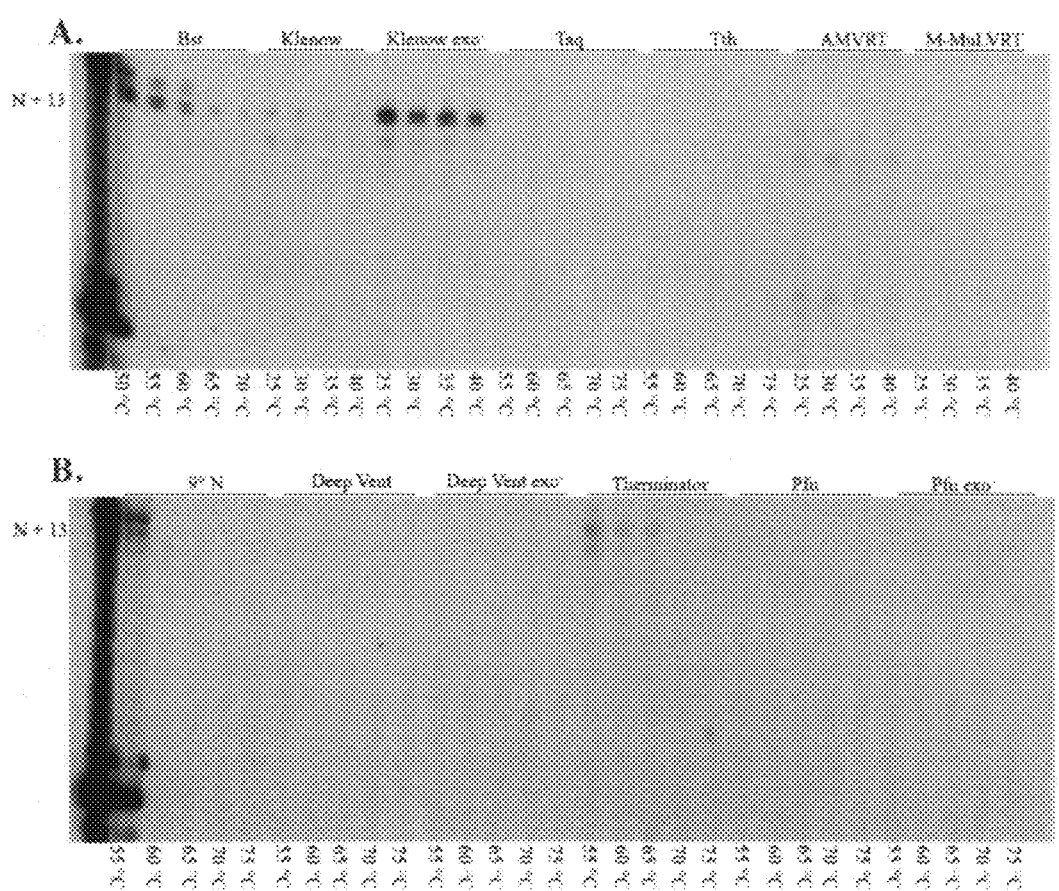
FIG. 15. Seeking a 3'-terminal fragment that does not prime by itself. Screening polymerases for 8+6 extension with just the 3'-terminal fragment carrying a 5'-amino group. Final concentrations: dNTPs (100 µM each, for A, T, G, C, with 33 nM alpha $^{32}$P-dCTP), template (30 pmol, 3 µM), and 3'-terminal 6-mer fragment carrying a 5'-amino group (20 pmol, 2 µM). The mixtures containing the indicated polymerase were brought to the indicated temperature for 30 sec and dNTPs were added. The mixtures were incubated at the indicated temperatures for 2 min. Reactions were terminated with quench buffer (5 µl, formamide EDTA, dyes, dilution factor of 33%). An aliquot (1 µl) was loaded on a polyacrylamide gel (20%, 7 M urea) and resolved. The full length product is now N+13, because the primer is a 6-mer. Note that the synthesis of full length product with Klenow is almost certainly due to the fact the temperature is lower. Only the Therminator polymerase effectively extends the shorter primer.
Figure 16:
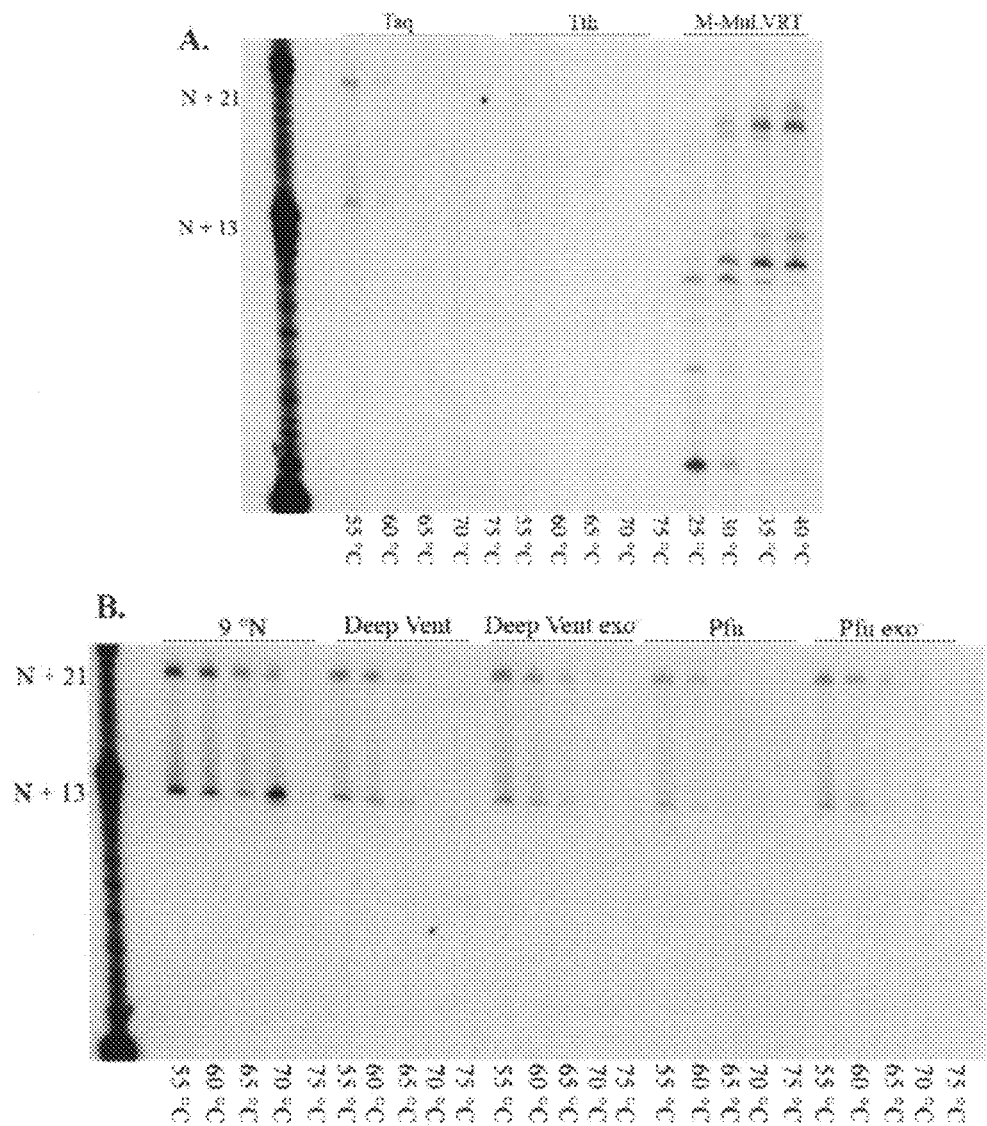
FIG. 16. Extension of a composite primer assembled from 8-mer and 6-mer fragments on a DNA 38-mer template. Final concentrations: dNTPs (100 μM each, for A, T, G, C, with 33 nM alpha $^{32}$P-dCTP) template (30 pmol, 3 μM), 3'-terminal 6-mer fragment carrying a 5'-amino group (20 pmol, 2 μM) and 5'-terminal 8-mer carrying a 3'-CH$_2$CHO unit (20 pmol, 2 μM). The mixtures containing the indicated polymerase were brought to the indicated temperature for 30 sec and dNTPs were added. The mixtures were incubated at the indicated temperatures for 2 min. Reactions were terminated with quench buffer (5 μl, formamide EDTA, dyes, dilution factor of 33%). An aliquot (1 μl) was loaded on a polyacrylamide gel (20%, urea 7 M) and resolved.
Figure 17:
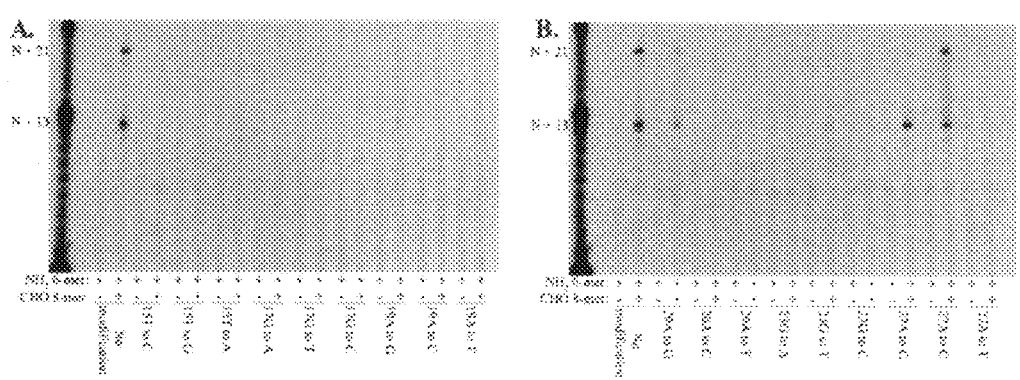
FIG. 17. Mismatched templates using 9° N. PAGE gel (20%) of primer extension assays with mismatched DNA 38-mer templates using 9° N. Final concentrations: dNTPs (100 μM each, for A, T, G, C, with 33 nM alpha $^{32}$P-dCTP) template (30 pmol, 3 μM), 3'-terminal 6-mer fragment carrying a 5'-amino group (20 pmol, 2 μM) and 5'-terminal 8-mer carrying a 3'-CH$_2$CHO unit (20 pmol, 2 μM). Reaction mixtures were brought to 70° C. for (30 sec), and dNTPs were added. The mixtures were incubated for 2 min at the appropriate temperature. Reactions were terminated with quench buffer (5 μl, formamide EDTA, dyes, dilution factor of 33%). An aliquot (1 μl) was loaded on a polyacrylamide gel (20%, urea 7 M) and resolved. Single nucleotide mismatches for the 3'-terminal fragment inhibits extension of primers to full length product (N+13 and N+21) (Panel A). Depending on the location of the mismatches in the 5'-fragment, decreased amounts of full length product (Panel B) are observed.

In this work, we may generate a library of three sets of 256 tetramers, the first set with a 5'-OH and a 3'-$CH_2$—CHO unit (the 5'-blocking fragment), the second set with a 5'-amino group and a 3'-OH unit linker (the 3'-blocking fragment), and the third set with both a 5'-amino group and a 3'-$CH_2$—CHO unit (the connector fragments), to generate fragments that complement whatever templating DNA or RNA is available. The assembly of multiple structures leads to products of the type shown in FIG. 10. While in principle, k can be indefinitely large, the presently preferred number of units assembled, if greater than 2, is not greater than 10.

The number and length depends in large part upon the degree to which the imine $CH_2$—CH=NH—$CH_2$ linker supports Watson-Crick pairing. In the extreme, there is little doubt that very long fragments (m and n are both >10) can be linked indefinitely into long segments. On the other hand, the shorter the sequences, the more valuable the ligation will be to support searching for sequences where the sequence being sought is not known to be present.

Example 5

The synthesis of a PNA that is terminated at the carboxyl end with an aldehyde is performed on the solid phase. Controlled pore glass carrying an amino functionality is treated with p-nitrobenzoyl chloride in pyridine to make the p-nitrophenyl amide. The support is then thoroughly washed with water until the pH of the washings is neutral. The support is then treated with a solution of aqueous stannous chloride (0.2 M, 40° C., with HCl 1 M) to convert the nitro groups to amino groups. The support is then thoroughly washed with water until the pH of the washings is greater than 5. The number of amino groups per gram of support is then determined, and this value is taken as "one equivalent" for the next steps.

The support is then suspended in ethanol at 0° C. To the suspension is added two equivalents of isoamyl nitrite in ethanol. The mixture is allowed to incubate at 0° C. for 2 hours, to convert the support-bound amine groups to their corresponding diazonium salts.

The support is then thoroughly washed, and then treated with an aqueous solution of sodium sulfide ($EtOCS_2$ is also satisfactory) at room temperature for two hours. This step converts the phenylamino groups to support-bound phenyl-SH groups.

Other methods known in the art for preparing a support-bound phenyl-SH unit are equally acceptable.

The support is then treated with a solution of chloroacetaldehyde (Aldrich 31727-6) in a 1:1 mixture of methanol in water at 0° C. for 20 min. The support is then thoroughly washed. This generates a support having phenyl-S—$CH_2$CHO units attached. The level of aldehyde is then determined, and this value is taken as "one equivalent" for the remaining steps.

This support is then treated following the method of [Wil95] with a solution of diaminoethane (20 equivalents) in methanol:water mixtures (1:1) at 0° C. To the mixture is then added sodium cyanoborohydride (20 equivalents in hydride), and the incubation is continued for 1 hour at room temperature. The solid support is recovered by filtration and thoroughly washed with methanol:water, with dilute acetic acid in methanol:water, and then with methanol:water until the pH of the washings was near neutral. This generates a support having phenyl-S—$CH_2CH_2$NH—$CH_2CH_2$—$NH_2$ units attached.

The support is then suspended in dimethylformamide (ca. 10 mL per gram of support), and the suspension is treated with triethylamine (0.1 mL per mL of formamide) and cooled to 0° C. Monomethoxytrityl chloride (MmtCl, 1 equivalent in methylene chloride) is then added, and the mixture is allowed to rise slowly to room temperature over 2.5 hours. The support is then thoroughly washed with DMT, and then methanol. This generates a support having phenyl-S—$CH_2CH_2$NH—$CH_2CH_2$—NH-Mmt units attached.

The support is then suspended in DMF. To the suspension is added HOOBt (5 equiv.) and NEM (10 equiv.) A solution of N-1-carboxymethylthymine [Wil95] (5 equiv.) dissolved in dimethylformamide is then added, followed by DIPC (7 equiv.). The mixture is stirred at room temperature for 20 hours. The mixture is then thoroughly washed.

For PNA analog sequences not ending in the thymine aldehyde, a preselected base-acetic acid (Base-$CH_2$—COOH) is added instead of N-1-carboxymethylthymine.

This generates a support having phenyl-S—$CH_2CH_2$N (CO—$CH_2$-T)-$CH_2CH_2$—NH-Mmt units attached. This material is now suitable for coupling using the procedure of Will et al. In this example, three sequential couplings are done, with a unit carrying protected cytosine, followed by coupling with a unit carrying protected adenine, followed by coupling with a unit carrying protected guanine, all known in the art [Wil95]. The coupling and capping steps are as described in [Wil95].

This generates a support having phenyl-S—$CH_2CH_2$N (CO—$CH_2$-T)-$CH_2CH_2$—NH—CO—$CH_2$N(CO—$CH_2$—$^P$C)—$CH_2CH_2$—NH—CO—$CH_2$N(CO—$CH_2$—$^P$A)-$CH_2CH_2$—NH—CO—$CH_2$N(CO—$CH_2$—$^P$G)-$CH_2CH_2$—NH-Mmt units attached, where the superscript "P" indicates the protecting groups used by Will et al. [Wil95].

The support is then treated at 10° C. with a solution of 10% aqueous hydrogen peroxide. This oxidizes the sulfide to a sulfoxide. The support is then suspended with stirring in a mixture of trifluoroacetic anhydride, trimethylpyridine, and acetonitrile at 0° C. following the procedure of Bravo et al. [Bra90]. This generates a support carrying phenyl-S—CH (OAc)$CH_2$N(CO—$CH_2$-T)-$CH_2CH_2$—NH—CO—$CH_2$N (CO—$CH_2$—$^P$C)—$CH_2CH_2$—NH—CO—$CH_2$N(CO—$CH_2$—$^P$A)-$CH_2CH_2$—NH—CO—$CH_2$N(CO—$CH_2$—$^P$G)-$CH_2CH_2$—NH-Mmt units. The support is thoroughly washed. If the Mmt group is lost, it may be replaced.

After the synthesis is complete, the support is treated with concentrated aqueous ammonia, following the procedure of Will et al. [Wil95], generating a support having phenyl-S—CH(OH)$CH_2$N(CO—$CH_2$-T)-$CH_2CH_2$—NH—CO—$CH_2$N (CO—$CH_2$—C)—$CH_2CH_2$—NH—CO—$CH_2$N(CO—$CH_2$-A)-$CH_2CH_2$—NH—CO—$CH_2$N(CO—$CH_2$-G)-$CH_2CH_2$—NH-Mmt units attached. The phenyl-S—CH (OH) linkage is unstable over time under these conditions, and CHO—$CH_2$N(CO—$CH_2$-T)-$CH_2CH_2$—NH—CO—$CH_2$N(CO—$CH_2$—C)—$CH_2CH_2$—NH—CO—$CH_2$N (CO—$CH_2$-A)-$CH_2CH_2$—NH—CO—$CH_2$N(CO—$CH_2$-G)-$CH_2CH_2$—NH-Mmt is released. To initiate the template directed equilibrium coupling, the material can be treated with 80% formic acid, the formic acid removed by freeze drying, and the coupling initiated by delivering the material to a solution containing the template DNA having the sequence 5'-AGTCAGTC buffered at pH 7.

LITERATURE CITED

[Bag96] Bag, B. G., von Kiedrowski, G. (1996) Templates, autocatalysis and molecular replication. *Pure Appl. Chem.* 68, 2145-2152

[Ben04] Benner, S. A. (2004) Understanding nucleic acids using synthetic chemistry. *Acc. Chem. Res.* 37, 784-797

[Ben95] Benner, S. A. (1995) Receptor Assisted Combinatorial Chemistry. U.S. Pat. No. 5,958,702. Filing date: Feb. 6, 1995

[Bog99] Bogan J, Ignatovich L, Stankevich E (1999) Reversed (5'→3') oligonucleotide synthesis on oxalyl-CPG support. *Nucleosides Nucleotides Nucl. Acids* 18, 1183-1185

[Bra90] Bravo, P., Frigerio, M., Resnati, G. (1990) Synthesis of (s) beta,beta,beta trifluorolactic acid and (s)-alpha-methoxy-alpha(trifluoromethyl) phenylacetic acid from (R) methyl p-tolyl sulfoxide. *J. Org. Chem.* 55, 4216-4218.

[Car95] Carell, T., Wintner, E. A., Sutherland, A. J., Rebek, J., Dunayevskiy, Y. M., Vouros, P. (1995) New promise in combinatorial chemistry. Synthesis, characterization, and screening of small-molecule libraries in solution. *Chem. Biol.* 2, 171-183

[Chu89] Chu, C. K., Doboszewski, B., Schmidt, W., Ullas, G. V. (1989) Synthesis of pyrimidine 3'-allyl-2',3'-dideoxyribonucleosides by free-radical coupling. *J. Org. Chem.* 54, 2767-2769

[Des94] Desai, M. C., Zuckermann, R. N., Moos, W. H. (1994) Recent advances in the generation of chemical diversity libraries. *Drug Devel. Res.* 33, 174-188

[Ell96] Ellman, J. A. (1996) Design, synthesis, and evaluation of small-molecule libraries. *Accounts Chem. Res.* 29, 132-143

[Erl100] Erlanson, D. A., Braisted, A. C., Raphael, D. R., Randal, M., Stroud, R. M., Gordon, E. M., Wells, J. A. (2000) Site-directed ligand discovery. *Proc. Natl. Acad. Sci. USA* 97, 9367-9372

[Esc98] Eschgfäller, B., König, M., Boess, F., Boelsterli, U. A., Benner, S. A. (1998) Synthesis and biodistribution of a short non-ionic oligonucleotide analog in mouse. *J. Med. Chem.* 41, 276-283

[Fel94] Felder, E. R. (1994) The challenge of preparing and testing combinatorial compound libraries in the fast lane. At the front-end of drug development. *Chimia* 48, 531-541

[Gig98] Giger, T., Wigger, M., Audétat, S., Benner, S. A. (1998) Libraries for receptor-assisted combinatorial synthesis (RACS). The olefin metathesis reaction. *SynLett* 6, 688-692

[Goo92] Goodwin, J. T., Lynn, D. G. (1992) Template-directed synthesis. Use of a reversible-reaction. *J. Am. Chem. Soc.* 114, 9197-9198

[Gor 94] Gordon, E. M., Barrett, R. W., Dower, W. J., Fodor, S. P. A., Gallop, M. A. (1994) Applications of combinatorial technologies to drug discovery 0.2. combinatorial organic-synthesis, library screening strategies, and. future-directions. *J. Med. Chem.* 37, 1385-1401

[Hou91] Houghton, R. A., Pinilla, C., Blondelle, S. E., Appel, J. R., Dooley, C. T., Cuervo, J. H. (1991) Generation and use of synthetic peptide combinatorial libraries for basic research and drug discovery. *Nature* 354, 84-87

[Huc97] Huc, I., Lehn, J. M. (1997) Virtual combinatorial libraries: Dynamic generation of molecular and supramolecular diversity by self-assembly. *Proc. Natl. Acad. Sci., USA* 94, 2106-2110.

[Hut02] Hutter, D., Blaettler, M. O., Benner, S. A. (2002) From phosphate to dimethylenesulfone: Non-ionic backbone linkers in DNA. *Helv. Chim. Acta.* 85, 2777-2806

[Jam97] James, K. D., Ellington, A. D. (1997) Surprising fidelity of template-directed chemical ligation of oligonucleotides. *Chem. Biol.* 4, 595-605.

[Jam98] James, K. D., Boles, A. R., Henckel, D., Ellington, A. D. (1998) The fidelity of template-directed oligonucleotide ligation and its relevance to DNA computation. *Nucl. Acids. Res.* 26, 5203-5211

[Jam99] James, K. D, Ellington, A. D. (1999) The fidelity of template-directed oligonucleotide ligation and the inevitability of polymerase function (1999) *Origins Life Evol. Biosphere* 29, 375-390

[Lam91] Lam, K. S., Salmon, S. E., Hersh, E. M., Hruby, V. J., Kazmierski, W. M., Knapp, R. J. (1991) A new type of synthetic peptide library for identifying ligand binding activity. *Nature* 354, 82-84

[Leh01] Lehn, J.-M., Ramstrom, O. Bunyapaiboonsri, T. Application Ser. No. 10/363,638. PCT filed Sep. 4, 2001, PCT/EP01/10170 Generation of combinatorial libraries and assessment thereof by deconvolution., Published as 20040029172]

[Leh01] Lehn, J.-M., Ramstrom, O. Application Ser. No. 10/220,470. PCT filed Mar. 1, 2001, PCT/EP01/02310 Generation and screening of a dynamic combinatorial library. Published as US200400434171

[Luo98] Luo, P., Leitzel, J. C., Zhan, Z.-Y. J., Lynn, D. G. (1998) Analysis of the structure and stability of a backbone-modified oligonucleotide: Implications for avoiding product inhibition in catalytic template-directed synthesis. *J. Am. Chem. Soc.* 120, 3019-3031

[Lut97] Lutz, M. J., Benner, S. A., Hein, S., Breipohl, G., Uhlmann, E. (1997) Recognition of uncharged polyamide-linked nucleic acid analogs by DNA polymerases and reverse transcriptases. *J. Am. Chem. Soc.* 119, 3177-3178

[Nie91] Nielsen P E, Egholm M, Berg R H, Buchardt O (1991) Sequence-Selective Recognition of DNA by Strand Displacement with a Thymine-Substituted Polyamide," *Science* 254, 1497-1500

[Pom02] Pomeroy, S. L., Tamayo, P., Gaasenbeek, M., Sturla, L. M., Angelo, M., McLaughlin, M. E., Kim, J. Y. H., Goumnerova, L. C., Black, P. M., Lau, C., Allen, J. C., Zagzag, D., Olson, J. M., Curran, T., Wetmore, C., Biegel, J. A., Poggio, T., Mukherjee, S., Rifkin, R., Califano, A., Stolovitzky, G., Louis, D. N., Mesirov, J. P., Lander, E. S., Golub, T. R. (2002) Prediction of central nervous system embryonal tumour outcome based on gene expression. *Nature* 415, 436-442

[Ram02] Ramstrom O, Lehn J M (2002) Drug discovery by dynamic combinatorial libraries. *Nature Reviews Drug Discovery* 1, 26-36

[Ram04] Ramstrom O, Lohmann S, Bunyapaiboonsri T, et al. (2004) Dynamic combinatorial carbohydrate libraries: Probing the binding site of the concanavalin A lectin. *Chemistry—A European Journal* 10, 1711-1715

[Ran04] Rando, R. F., Welch, E. Methods for identifying small molecules that bind specific RNA structural motifs. U.S. Ser. No. 10/475,024; PCT Filed: Apr. 11, 2002, PCT/US02/11757 Published as 20040219545 Nov. 4, 2004

[San04] Sando, S., Abe, H. and Kool, E. T. (2004) Quenched auto-ligating DNAs: Multicolor identification of nucleic acids at single nucleotide resolution. *J. Am. Chem. Soc.* 126, 1081-1087

[Sie94] Sievers, D., von Kiedrowski, G. (1994) Self replication of complementary nucleotide-based oligomers. *Nature* 369, 221-224

[Uhl00] Uhlmann; Eugen, Breipohl; Gerhard, Benner; Steven A., Lutz; Michael. Process for amplifying nucleic acids using DNA/PNA primers Filed: Sep. 11, 1997 Issued as U.S. Pat. No. 6,063,571 on May 16, 2000

[Uhl97] Uhlmann E, Will D W, Breipohl G, Peyman A, Langner D, Knolle J, OMalley G (1997) Synthesis of polyamide nucleic acids (PNAs), PNA/DNA-chimeras and phosphonic ester nucleic acids (PHONAs) *Nucleosides & Nucleotides* 16 (5-6): 603-608

[Uhl97] Uhlmann E, Will D W, Breipohl G, Peyman A, Langner D, Knolle J, OMalley G (1997) Synthesis of polyamide nucleic acids (PNAs), PNA/DNA-chimeras and phosphonic ester nucleic acids (PHONAs) *Nucleosides & Nucleotides* 16, 603-608

[Wig02] Wigger, M., Eyler, J. R., Benner, S. A., Li, W., Marshall, A. G. (2002) FT-ICR mass spectrometric resolution, identification, and screening of noncovalent complexes of Hck SH2 domain receptor and ligands from a 324 peptide combinatorial library. *J. Am. Soc. Mass Spect.* 13, 1162-1169

[Wig97] Wigger, M., Nawrocki, J. P., Watson, C. H., Eyler, J. R., Benner, S. A. (1997) Assessing enzyme substrate specificity using combinatorial libraries and electrospray ionization Fourier transform ion cyclotron resonance mass spectrometry. *Rapid Commun. Mass Spect.* 11, 1749-1752

[Wil95] Will, D. W., Langner, D., Knolle, J., Uhlmann, E. (1995) The Synthesis of Polyamide Nucleic-Acids Using a Novel Monomethoxytrityl Protecting-Group Strategy. *Tetrahedron* 51 (44): 12069-12082.

[Woo03] Woods, K. K., Lan, T., McLaughlin, L. W., Williams, L. D. (2003) The role of minor groove functional groups in DNA hydration. *Nucl. Acids Res.* 31, 1536-1540

[Zha01] Zhan, Z.-Y. J., Ye, J. D., Li, X. Y., Lynn, D. G. (2001) Replicating DNA differently. *Curr. Org. Chem.* 5, 885-902.

[Zha05] Zhang, L., Peritz, A., Meggers, E. (2005) A simple glycol nucleic acid. *J. Am. Chem. Soc.* 127, 4174-4175.

[Zha97] Zhang, M. (1997). Identification of protein coding regions in the human genome by quadratic discriminant analysis. *Proc. Natl. Acad. Sci.* 94, 565-568

What is claimed is:

1. The process of preparing a nucleic acid analog that binds to a preselected template, said process comprising contacting a 3'-fragment molecule having a functional group at its 5'-terminus, at the same time as contacting a 5'-fragment molecule having a functional group at its 3'-terminus, where the 3'- and 5'-fragments are Watson-Crick complementary to and bind through Watson-Crick pairing to adjacent segments of a preselected linear template molecule, wherein said 5'- and 3'-fragments, bound to said template, form a product molecule by a reaction between the functional groups at their respective 3'- and 5'-terminii to form a covalent bond, wherein the formation of said covalent bond is reversible under the conditions where the contacting occurs.

2. The process of claim 1 wherein said product molecule serves as a primer for a DNA polymerase, an RNA polymerase, or a reverse transcriptase.

3. The process of claim 1 wherein said preselected template molecule is a DNA molecule or an RNA molecule.

4. The process of claim 1, wherein said fragment molecules are nucleic acid analogs selected from the group consisting of ribonucleic acid, 2'-O-methylribonucleic acid, 2'-deoxyribonucleic acid, locked nucleic acid, bicyclonucleic acid, peptide nucleic acid, or glycol nucleic acid.

5. The process of claim 1 wherein said product molecule is described by the formula

Figure 9:
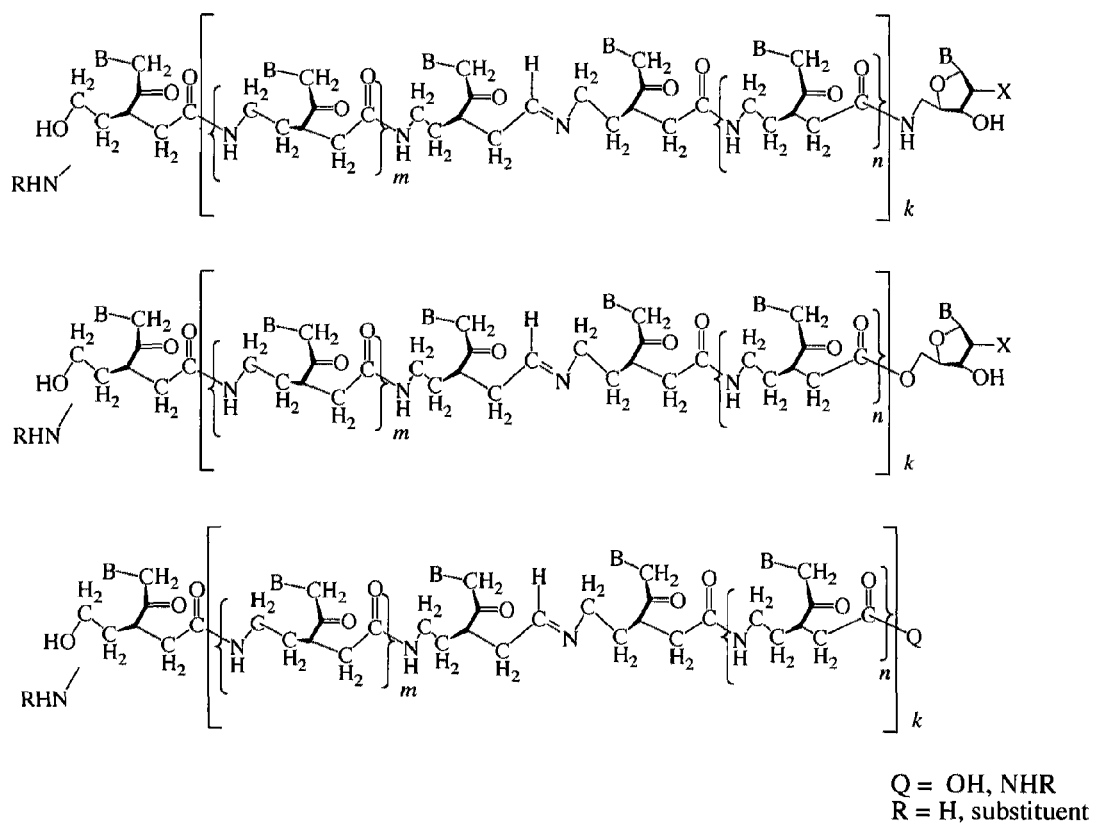
FIG. 9. The products that are formed through template-assembly of multiple fragments under dynamic equilibrium conditions. Unless the composites are to be used as the primer, the "3'-end" (note that the numbering in PNA is analogous to that in DNA, as the structures are shown) is not critical. The functionality at the 5'-end is never critical, and this end can have an —OH, amine, phosphate, or protected derivative R. As is known in the literature, the R groups are often chosen to enhance the solubility of the molecule (especially a PNA), or make it fluorescent.

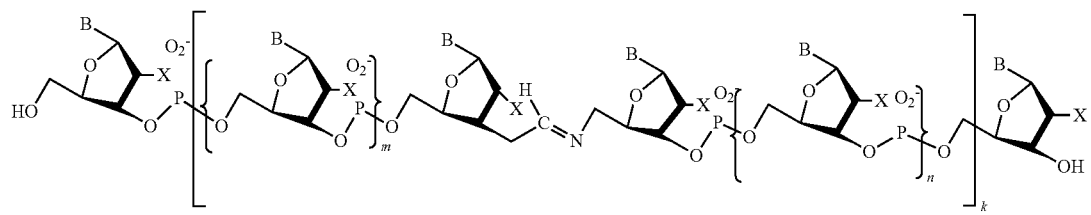

wherein X is selected from the group consisting of —H, —OH, —OCH$_3$, and —O-allyl, the B groups are heterocycles independently selected from the group consisting of adenine and the heterocycles in the structures shown in FIGS. 5, 7, and 9, k is an integer from 1 to 10, and m and n are integers between 2 and 13.

6. The process of claim 1, wherein said 3'- and 5'-fragment molecules are presented as libraries, each library comprising two or more fragments, which differentially join to form product molecules depending on the presence of a template, whose sequence is not preselected.

7. A process of preparing a nucleic acid analog that binds to a preselected template, said process comprising contacting a 3'-fragment molecule having a functional group at its 5'-terminus, at the same time as contacting a 5'-fragment molecule having a functional group at its 3'-terminus, where the 3'- and 5'-fragments are Watson-Crick complementary to and bind through Watson-Crick pairing to adjacent segments of a preselected linear template molecule, wherein said 5'- and 3'-fragments, bound to said template, form a product molecule by a reaction between the functional groups at their respective 3'- and 5'-terminii to form a covalent bond, wherein the formation of said covalent bond is reversible under the conditions where the contacting occurs, wherein said product molecule is

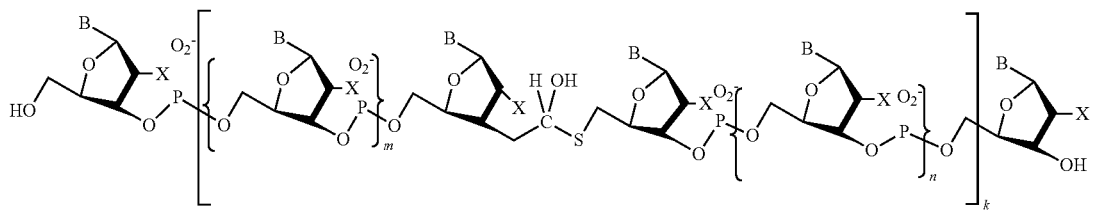

8. A process of preparing a nucleic acid analog that binds to a preselected template, said process comprising contacting a 3'-fragment molecule having a functional group at its 5'-terminus, at the same time as contacting a 5'-fragment molecule having a functional group at its 3'-terminus, where the 3'- and 5'-fragments are Watson-Crick complementary to and bind through Watson-Crick pairing to adjacent segments of a preselected linear template molecule, wherein said 5'- and 3'-fragments, bound to said template, form a product molecule by a reaction between the functional groups at their respective 3'- and 5'-terminii to form a covalent bond, wherein the formation of said covalent bond is reversible under the conditions where the contacting occurs, wherein said product molecule is wherein X is selected from the group consisting of —H, —OH, —OCH$_3$, and —O-allyl, the B groups are heterocycles independently selected from the group consisting of adenine and the heterocycles in the structures shown in FIGS. 5, 7, and 9, k is an integer from 1 to 10, and m and n are integers between 2 and 13.

9. A process of preparing a nucleic acid analog that binds to a preselected template, said process comprising contacting a 3'-fragment molecule having a functional group at its 5'-terminus, at the same time as contacting a 5'-fragment molecule having a functional group at its 3'-terminus, where the 3'- and 5'-fragments are Watson-Crick complementary to and bind through Watson-Crick pairing to adjacent segments of a pre-

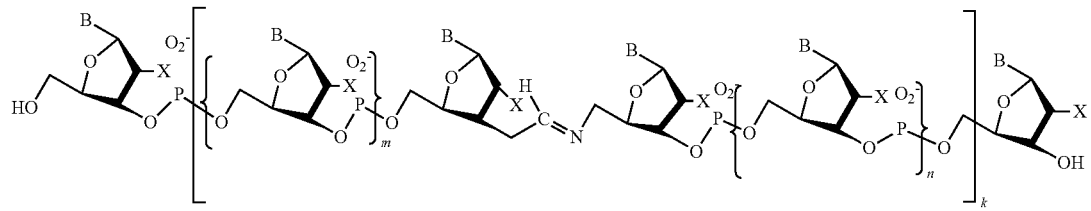

wherein X is selected from the group consisting of —H, —OH, —OCH$_3$, and —O-allyl, the B groups are heterocycles independently selected from the group consisting of adenine and the heterocycles in the structures shown in FIGS. 5, 7, and 9, k is an integer from 1 to 10, and m and n are integers between 2 and 13.

selected linear template molecule, wherein said 5'- and 3'-fragments, bound to said template, form a product molecule by a reaction between the functional groups at their respective 3'- and 5'-terminii to form a covalent bond, wherein the formation of said covalent bond is reversible under the conditions where the contacting occurs, wherein said product molecule is selected from the group consisting of

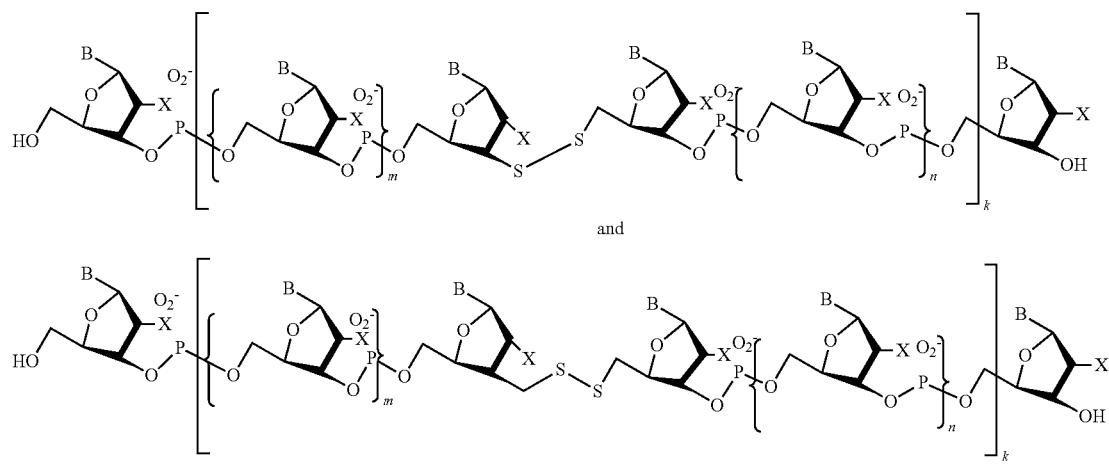
wherein X is selected from the group consisting of —H, —OCH₃, and —O-allyl, the B groups are heterocycles independently selected from the group consisting of adenine and the heterocycles in the structures shown in FIGS. 5, 7, and 9, k is an integer from 1 to 10, and m and n are integers between 2 and 13.
\* \* \* \* \*